US007353238B1

(12) United States Patent
Gliklich

(10) Patent No.: US 7,353,238 B1
(45) Date of Patent: Apr. 1, 2008

(54) APPARATUS AND METHODS FOR DETERMINING AND PROCESSING MEDICAL OUTCOMES

(75) Inventor: Richard E. Gliklich, Boston, MA (US)

(73) Assignee: Outcome Sciences, Inc., Cambridge, MA (US)

(*) Notice: Subject to any disclaimer, the term of this patent is extended or adjusted under 35 U.S.C. 154(b) by 0 days.

(21) Appl. No.: 09/330,384

(22) Filed: Jun. 11, 1999

Related U.S. Application Data

(60) Provisional application No. 60/089,183, filed on Jun. 12, 1998, provisional application No. 60/089,114, filed on Jun. 12, 1998.

(51) Int. Cl.
*G06F 17/00* (2006.01)
*G06F 7/00* (2006.01)

(52) U.S. Cl. .................................. 707/104.1; 705/2
(58) Field of Classification Search ............. 705/1, 705/2, 3; 600/300, 301; 700/91; 707/104.1
See application file for complete search history.

(56) References Cited

U.S. PATENT DOCUMENTS

| 5,715,449 | A |   | 2/1998  | Peters, Jr. et al. ......... 395/613 |
| 5,737,539 | A | * | 4/1998  | Edelson et al. ................ 705/2 |
| 5,924,073 | A | * | 7/1999  | Tyulaman et al. .......... 600/300 |
| 5,991,728 | A | * | 11/1999 | DeBusk et al. ................ 705/2 |
| 6,108,635 | A | * | 8/2000  | Herren et al. ................. 705/2 |
| 6,151,581 | A | * | 11/2000 | Kraftson et al. ............. 705/3 |
| 6,151,586 | A | * | 11/2000 | Brown ........................... 705/2 |
| 6,190,313 | B1 | * | 2/2001 | Hinkle et al. ............... 600/300 |
| 6,196,970 | B1 | * | 3/2001 | Brown ......................... 600/300 |
| 6,223,164 | B1 | * | 4/2001 | Seare et al. ................... 705/2 |
| 6,246,992 | B1 | * | 6/2001 | Brown ........................... 705/2 |
| 6,266,675 | B1 | * | 7/2001 | Evans et al. ............. 707/104.1 |
| 6,272,468 | B1 | * | 8/2001 | Melrose ......................... 705/2 |

OTHER PUBLICATIONS

"American Medical Accreditation Program Criteria for AMAP-compatible Physician Performance Measurement Systems," Working Document—Copyright Feb. 19, 1999, American Medical Association.

* cited by examiner

*Primary Examiner*—Sam Rimell
(74) *Attorney, Agent, or Firm*—Chapin IP Law, LLC; Barry W. Chapin, Esq.

(57) ABSTRACT

A data processing system is provided for determining clinical outcomes of medical data gathered by the system. The system can allow a person to define a medical study and can then administer the medical study and can collect and analyze data from potentially geographically diverse doctors, patients and other people associated with a study. Users enter sets of medical information. The system can analyze the medical data according to any number of clinical algorithms that may be custom defined and edited before and during the study. The system conditionally outputs the clinical outcome to the user. The clinical outcome can be used for treatment of patients participating in the study immediately after the data is input and analyzed. The medical outcomes can indicate such things as performance comparisons, composite outcomes, and risk stratification and assessments for such things as treatments, drugs, illnesses, doctors, patients and physician groups.

30 Claims, 24 Drawing Sheets

Outcome Sciences – Healthcare Consulting – Netscape

File  Edit  View  Go  Communicator  Help

Back  Forward  Reload  Home  Search  Guide  Print  Security  Stop

Bookmarks  Location: http://www.outcomesciences.com/data/demo1.html

Internet  Lookup  New&Cool

Data Entry | Review Data | Email US | Home

Welcome Dr. Gliklich

Physician ID: 172
Study ID: 5409

| Patient Id# | Initial | 3 Month | 6 Month | 12 Month |
|---|---|---|---|---|
| Enter New Patient | | | | |
| 4351 | x | x | x | next |
| 4352 | x | x | next | x |
| 4353 | x | next | x | x |
| 4354 | x | x | x | next |
| 4355 | x | x | x | next |
| 4356 | x | x | x | next |

Outcome Sciences – Healthcare Consulting – Netscape — 825

Data Entry | Review Data | Email US | Home

Study Name: Breast Care    Physician ID: 1234567    Enter New Patient    Print all Forms ⎬ 882
*Italic* Text=Upcoming.  Regular Text=Done.   ■ Overdue — 883
— 884                                                    — 884

| SAE* | Patient Id# | Initial | Biopsy | Re-Biopsy | 6 Month | Surg Path |
|---|---|---|---|---|---|---|
| SAE 0 | chris | Initial | *Biopsy* | *if performed* | *11/03/1999* | *path* |
| SAE 0 | megan | Initial | *Biopsy* | *if performed* | *11/03/1999* | *path* |

821 — 822a — 822b — 822c — 822d — 881

Outcome Sciences – Healthcare Consulting – Netscape

File  Edit  View  Go  Communicator  Help

Back  Forward  Reload  Home  Search  Guide  Print  Security  Stop

Bookmarks  Location: http://www.outcomesciences.com/data/demo1.html

Internet  Lookup  New&Cool

Data Entry | New&Cool / Review Data | Email US | Home

⎯ 830

⎯ 831

Physician: Dr. Richard Gliklich
Physician ID: 172
Study ID: 5409
Patient ID: 4351

PHYSICAL WELL-BEING                                                                              *12mth*

|   |                                                                              | not at all | a little bit | somewhat | quite a bit | very much |
|---|------------------------------------------------------------------------------|------------|--------------|----------|-------------|-----------|
| 1. | I have a lack of energy                                                     | ○ 0        | ○ 1          | ○ 2      | ○ 3         | ○ 4       |
| 2. | I have nausea                                                               | ○ 0        | ○ 1          | ○ 2      | ○ 3         | ○ 4       |
| 3. | Because of my physical condition, I have trouble meeting the needs of my family | ○ 0        | ○ 1          | ○ 2      | ○ 3         | ○ 4       |
| 4. | I have pain                                                                 | ○ 0        | ○ 1          | ○ 2      | ○ 3         | ○ 4       |
| 5. | I am bothered by side effects of                                            | ○ 0        | ○ 1          | ○ 2      | ○ 3         | ○ 4       |

| | | | |
|---|---|---|---|
| | | | 12mth |

Data Entry | Review Data | Email US | Home |

7. Ulcer or gastrointestinal bleeding (not counting hemorrhoids? ○ Yes ○ No
8. Arthritis or rheumatism ○ Yes ○ No
9. Sciatica or chronic back pain? ○ Yes ○ No Has a doctor ever told you that you had any of the following conditions?

10. Hypertension or high blood pressure? ○ Yes ○ No
11. Angina? ○ Yes ○ No
12. Heart attack or myocardial infarction? ○ Yes ○ No
13. Stroke? ○ Yes ○ No
14. Kidney disease? ○ Yes ○ No
15. Cancer (not counting skin cancer)? ○ Yes ○ No Submit Form | Clear Form

Composite Outcome

|  | Pre-Tx | Post Tx |
|---|---|---|
| Site 24 | 52 | 85 |
| Total | 55 | 82 |
| Reference | 56 | 77 |

Back to Top

FIG. 16B

Stage-Comorbidity Strata for Site

|  | Site 24 | Total |
|---|---|---|
| Alpha | 10% | 45% |
| Beta | 40% | 45% |
| Gamma | 40% | 10% |

Back to Top

FIG. 16C

QOL By SF-36

|    | Pre-RX | Post-RX |
|----|--------|---------|
| PF | 62 | 79 |
| RP | 63 | 82 |
| BP | 46 | 72 |
| GH | 50 | 61 |
| VT | 54 | 57 |
| SF | 72 | 84 |
| RE | 74 | 79 |
| MH | 70 | 75 |

Back to Top

FIG. 16D

Patient Satisfaction Survey

Site 24        52        70
Total          54        56
Reference      52        52

Back to Top

FIG. 16E

Case Rate: Cost per Case by Strata and Site

|        | Alpha  | Beta   | Gamma  |
|--------|--------|--------|--------|
| Site 24 | 16,000 | 39,000 | 62,000 |
| All    | 14,000 | 34,000 | 78,000 |

Cost per Case by Risk Strata and Site: Year 1

Back to Top

FIG. 16F

APPARATUS AND METHODS FOR DETERMINING AND PROCESSING MEDICAL OUTCOMES

CO-PENDING RELATED APPLICATIONS AND CLAIM TO BENEFIT OF FILING DATE OF CO-PENDING RELATED APPLICATIONS

The below described invention is related to the subject matter, and claims the benefit of the filing date of the following now abandoned provisional patent applications of the same assignee as the present invention, the contents and teachings of which are incorporated herein by reference in their entirety:

Title: METHOD AND APPARATUS FOR MEDICAL COLLECTION AND REPORTING

Inventor: Dr. Richard E. Gliklich
U.S. Application No.: 60/089,183
Filing Date: Jun. 12, 1998

Title: METHOD AND APPARATUS FOR SYNCGHRONIZED CLIENT-SERVER TESTING AND DATA ACQUISITION Inventor: Dr. Richard E. Gliklich
U.S. Application No.: 60/089,114
Filing Date: Jun. 12, 1998

BACKGROUND OF THE INVENTION

Medical outcomes research is routinely performed and often mandated within the medical community. The goal of such research is to evaluate various factors which effect the health, well-being and medical treatment for people in society. Medical outcomes research can exist in many forms. By way of example, such research can include the evaluation of drugs, ailments, diseases, doctors, treatment techniques, and so forth in relation to various factors such as recovery rates, costs, incidences of sickness, side effects, patient mortality and/or other factors. Specific clinical or medical studies are often used to conduct medical outcomes research, as a way of gathering data related to the specific medical topic being researched.

Generally, to conduct a medical study on a specific medical topic, medical professionals such as doctors and other allied health professionals, and sometimes selected patients involved in the study, provide medical information related to the topic of the study which is being researched. The medical information gathered is often general in nature and may be obtained, for example, by reviewing patient records maintained in a hospital. Due to various reasons, information that can be obtained may be limited to only relevant factors within the patient files, and often excludes extraneous information that is not considered related to the medical study. Once the medical information from these various sources is gathered, the information is reviewed by a person in charge of conducting the study. The reviewer collates the information into various categories of data, which are collectively called medical outcomes for the study. Typically, the medical outcomes provide an indication, score or other criteria, based on the data collected in the study which may indicate, determine or evaluate the effectiveness or performance of a doctor, drug, or medical treatment as related to the treatment of a disease, sickness or other malady.

As an example, a drug manufacturer may sponsor a medical outcomes study to determine the effectiveness of a new drug recently released into use for the medical treatment of a specific ailment. The drug manufacturer may commission a medical research institute or other entity to research how many prescriptions of the drug have been filled, and of those filled prescriptions, how many of the patients who took the drug have successfully recovered from the disease. This information may be gathered over a long period of time across a wide range of the population. Once the information has been collected, the entity conducting the study can analyze the data that was collected to determine recovery rates for patients who took the drug. As a specific example, if ten thousand prescriptions of the drug were filled over a three year period, and seven thousand patients who took the drug experienced positive results from the drug treatment, the clinical outcome produced as a result of the research may indicate that the drug has a seventy percent effectiveness rating. The researching organization can then publish this clinical outcome in a report to inform the medical population and the public at large about the past performance of the drug in relation to its effectiveness in treating a disease.

More detailed information on prior art techniques for conducting medical outcome studies and research is available in the text entitled "Medical Outcomes & Guidelines Sourcebook", published in 1998 in the United States by Faulkner & Gray's Healthcare Information Center, Eleven Penn Plaza, New York, N.Y., the contents of which is hereby incorporated by reference in its entirety.

SUMMARY OF THE INVENTION

Prior art techniques and methodologies for conducting medical outcomes research are fraught with deficiencies. Embodiments of the present invention are based, in part, on the recognition of these deficiencies and provide solutions to advance the state-of-the-art in medical outcomes research. A unique system and methodologies are disclosed herein for implementing, tracking, and processing medical outcomes research studies to produce clinical outcomes which result in a better understanding of medical and health care knowledge related to the treatment of sicknesses, illness, and disease and the treatment and performance of doctors, treatment techniques (e.g., surgical techniques), drugs and other related medical research interests.

Prior art medical study implementation techniques are largely general in nature with respect to the level of detail collected for the study. Generally, implementation of a study involves collecting data on forms which are filled out by doctors or medical directors of physicians groups. For example, in a drug study, a form may request information about how many prescriptions of a particular drug have been given over the past six months, and of those written, how many have resulted in positive patient outcomes. This information may be gathered over time from a large percentage of the medical population that prescribed the drug. The data may be collected over the course of many months or years, and once complete, the data is analyzed, possibly with the assistance of a computer or database, and a medical outcome is determined that gives a fairly accurate representation of the effectiveness of the drug at treating a particular illness. While such implementations of studies may seem quite complete, vast amounts of data remain unrecorded or, if recorded, remain unanalyzed in the study research, and are thus not considered in the study results or outcomes. For instance, detailed histories of every patient who took the drug are not analyzed in a large study due to the amount of time that would be required for such analysis. Using prior art medical study implementation techniques, it would be unrealistic to consider all information gained from every patient in the study.

Moreover, doctors themselves could provide a potentially large amount of information concerning the actual use of a drug being studied. However, prior art study techniques rarely account for a detailed analysis of the background and actions of every doctor who administers the drug in the study. Due the lack of detailed analysis of data in such prior art studies, the studies results may seem to accurately reflect the effectiveness of the drug, but there may be missing information making the results somewhat less accurate than if all data were to be considered in determining a particular outcome.

Another problem with prior art medical study implementation techniques is that the study results are made available long after the actual treatment of most patients that participate in the study. Thus, if a prior art study technique does gather data at the patient level, patient input is not used for study results that can then be used to treat those patients at that moment. More likely, the patient may have either fully recovered, or worse, may have died, before the results of the study can be used to benefit the patient population at large. In other words, prior art study techniques gather data over long periods of time, and once the data is gathered, at the end of the study, it is tabulated and a medical outcome is produced. The medical outcome may be beneficial at that time, but has little effect or benefit on the treatment of those individuals who partook in the study. Essentially, prior art study techniques are retrospective in that they produce information that benefits future patients, but offers little benefit to the patients, researchers, and doctors involved during the study.

Conversely, the present invention provides a system to implement and conduct medical studies to produce medical outcomes that can be used to treat patients that are currently participating in the study. That is, clinical outcome data produced from the system of the invention can be generated at any time, and in real-time, during the study. The medical outcome data is thus available for treatment of patients and can take into account all data entered by a doctor, patient, or other participant in the study, no matter where that person is geographically located. Thus, clinical outcomes produced from the system of the invention reflect the most up-to-date progress and results of the study.

Moreover, the granularity at which data is collected in studies administered by the clinical outcome system of the invention allows many more factors (than prior art systems) to be analyzed when generating medical outcome data. Data is collected on a patient by patient and doctor by doctor level, which allows cross-correlations of characteristics of medical data that were never before possible prior to the system of this invention.

More specifically, the present invention provides an embodiment comprising a clinical outcome system in the form of a digital data processing system for determining clinical outcomes of medical data. The digital data processing system includes an input mechanism receiving sets of medical information. Each set has characteristics relating to a specific medical study and the characteristics of each set also can have associated values. A storage mechanism is provided and is coupled to the input mechanism. The storage mechanism receives and maintains the sets of medical information. A processor is provided and is coupled to the storage mechanism. The processor selects a first characteristic common to at least two sets of medical information. The processor processes all values of the first characteristic according to a clinical algorithm to determine a clinical outcome of the sets of medical information for the specific medical study based upon the selected first characteristic. An output mechanism is also provided and is coupled to the processor to receive the clinical outcome of the sets of medical information and to output the clinical outcome to a user of the digital data processing system. The system allows use of the clinical outcome during the study based upon input received from the input mechanism. The clinical outcome may indicate, for example, a performance of a medical treatment, a doctor, and/or a drug in comparison to other medical treatments, doctors, and drugs and this indication may be used during progression of the study to treat patients, for example.

Also in accordance with the invention, the sets of medical information can contain characteristics related to the specific medical study and can include data related to a patient, a drug, an ailment, a doctor and a treatment technique. In such a configuration, the clinical outcome is determined based upon the selected first characteristic and indicates a statistical result derived from the clinical algorithm for at least one of the patient, drug, ailment, treatment or doctor in relation to another patient, drug, ailment, treatment and/or another doctor.

The processor in the clinical outcome system can also select a second characteristic common to the sets of medical information. The processor can process, using the clinical algorithm, the second characteristic in combination with the first characteristic to determine a cross-correlation between the first characteristic and the second characteristic which is included in the clinical outcome for the sets of medical information related to the specific medical study. This allows the invention to cross-correlate any information in the medical information to provide very detailed research results in the clinical outcome data.

For example, the first characteristic may be an identity of a doctor. In such a configuration, the clinical outcome can provide an indication of the performance of the doctor for a specific drug, a specific patient, and/or a specific ailment in comparison to other doctors. In another instance, the first characteristic may be an identity of at least one drug and the second characteristic may be an identity of another drug. As a result, the clinical outcome provides an indication of a performance of one drug for treating a patient in comparison to the other drug. In another instance, the first characteristic can be an identity of a first doctor and the second characteristic an identity of a second doctor. In this case, the clinical outcome can provide, for example, an indication of performance of the first doctor in comparison to the second doctor. The comparison can be related to i) treatment of a patient; ii) treatment of an ailment; iii) use of a drug; and/or iv) the success of a treatment (e.g. surgical technique).

Also in accordance with the invention, the processor instructs the input mechanism to receive specific sets of medical information based upon an identity of a user of the digital data processing system. In this case, the clinical algorithm for which all values of the first characteristic are processed is selected based upon the identity of the user of the digital data processing system. This allows the system to generate different clinical outcome data depending upon who is asking for the data.

The input mechanism may be coupled to a computer network including attached geographically diverse patient and doctor computer systems. In this case, the user of the digital data processing system can be a patient or doctor who enters at least one of the sets of medical information as input from a patient (or doctor) computer system which is remotely located from the digital data processing system. The output mechanism thus provides the clinical outcome to the patient (or doctor) over the network immediately after processing the data, thereby providing immediate feedback in response to entering patient data. This allows the data that was input, to be used, for example, in treatment of a patient at that moment.

In the system, the processor can analyze the clinical outcome for specific triggering events and can notify a doctor, a patient or other medical professional upon detection of a specific triggering event that is determined based on the analysis of the clinical outcome.

Other embodiments of the invention provide certain methods. Specifically, a method is provided for implementing medical studies, and includes the steps of selecting a medical study and entering medical data related to a patient associated with the medical study. Then, the method immediately processes the medical data entered in combination with other data associated with the medical study using a clinical algorithm specifically designed for the medical study to produce a clinical outcome of the medical study which takes into account the medical data entered that was related to the patient. The method can also immediately output the clinical outcome data once processed to provide an indication as to how the medical data that was entered effected the medical study, and can thus be used for immediate helpful insight that can be used, for example, to treat a patient or to determine how a doctor or drug is performing at that point in the study as compared to other doctors or drugs.

By immediately outputting the clinical outcome data, the method allows the clinical outcome data to be used to effect the present treatment of the patient based upon the medical data entered.

To select a medical study, the method of the invention includes the steps of obtaining an identification of an individual and presenting to the individual a list of medical studies for which that individual is associated, thereby focusing attention of the individual on particular medical studies. This saves, for example, a doctors time. The method also includes a step of allowing the user to select one of the medical studies for which that individual is associated, and, if the identification of the individual indicates the individual is a doctor, the method can present to the doctor a list of patients associated with the medical study and allows the doctor to select a patient associated with the medical study.

The method can immediately process the medical data entered using a clinical algorithm and can execute the clinical algorithm to produce such clinical outcome data as i) a comparison of doctors for treatment of an ailment; ii) a comparison of a drug for treatment of an ailment; iii) a comparison of a physician group for treatment of an ailment; and iv) a comparison of a surgical technique for treatment of an ailment.

To enter the medical data, the method includes the steps of presenting a first question related to the selected medical study to an individual and retrieving an answer to the question. Then, the method presents a second question related to the selected medical study to the individual. The second question presented may be determined by the answer retrieved in response to the first question. The method of the invention may then repeat the steps of presenting a first question, retrieving an answer and presenting a second question, such that a series of questions are presented to the individual which are governed by the answers received in response to former questions.

The method can also execute the clinical algorithm to determine if the medical data entered does not conform, within a predetermined threshold, to a standardized set of medical data associated with the medical study. If the data does not conform, the method can process a trigger event for an individual associated with the medical study. The trigger event may be processed for a doctor and the processor, in response to processing the trigger event, can notify the doctor that a patient has entered medical data that does not conform to the predetermined threshold of the standardized set of medical data associated with the medical study. The trigger event may also be processed for a patient. In this case, the processor, in response to processing the trigger event, notifies the patient that the patient has entered medical data that does not conform to the predetermined threshold of the standardized set of medical data associated with the medical study and that the patient should seek medical treatment. The trigger event can also be processed for a medical professional to detect, for example, the requirement for the prescription of a drug.

In accordance with another embodiment of the invention, a method is provided for performing medical diagnosis. This method receives sets of computerized medical study data and generates comparison results describing comparisons of the sets of computerized medical study data to produce a medical study profile (i.e. clinical outcome). Based on the medical study profile, the method provides an indication of a ranking of a characteristic of the medical study profile. The indication of the ranking can provide an indication of any set of computerized medical study data that contains a characteristic that does not conform, within a predetermined threshold, to a standardized characteristic in a typical set of computerized medical study data, thereby providing an indication of a need for further medical diagnosis of a patient associated with the set of computerized medical data containing the non-conforming characteristic. A trigger event can be generated for a patient and/or a doctor or other entity. The trigger event can notify the patient or the doctor or the entity of the non-conforming characteristic.

In this manner, feedback can be provided that can be used to effect treatment of a patient associated with the sets of computerized medical data that were received. Certain of the sets of computerized medical data may include a set of answers to a set of questions related to a particular person associated with the medical study. Also, the medical study profile may include a typical set of answers to the set of questions. In this case, the step of generating includes, for each set of computerized medical study data, a step of comparing the set of answers related to the particular person to the typical set of answers to the set of questions. As such, based upon the comparison of the set of answers to the typical set of answers, the method and system of the invention can provide a ranking indicative of a deviation of the set of answers from the typical set of answers.

As an example, the particular person may be a doctor and the ranking may indicate a relationship of the performance of the doctor in relation to the medical study data. The particular person may be a patient as well, and the ranking may indicate a level of treatment provided to the patient in relation to the medical study data.

Also provided as an embodiment of the invention is a computer program product having a computer-readable medium including computer program logic encoded thereon for determining clinical outcomes of medical data, such that the computer program logic, when executed on a processing unit with a computing device, causes the processing unit to perform the steps of the aforementioned methods of the invention. This embodiment is essentially software or code placed on or in a computer disk or memory that can execute in accordance with the teachings of this invention. This embodiment does not require the clinical outcome system to be a computer system or to have any hardware, circuitry or other tangible portion other than the software written in or onto a computer readable medium. The disk itself with the code that can operate according to the invention as explained herein is to be considered an embodiment of this invention, without a requirement that the code actually be compiled, or if already complied, there is no requirement that it be in execution.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 10A is a screen shot illustrating a web page interface used to select a patient and the next phase of a study for the patient according to an example embodiment of the invention.

FIG. 10B is a screen shot illustrating an alternative web page interface that can be used to select a patient and the next phase of a study for the patient according to an example embodiment of the invention.

FIGS. 11A and 11B are screen shots illustrating a web page interface used to gather a set of patient medical information according to an example embodiment of the invention.

FIG. 12 is a screen shot illustrating a web page interface that results if patient data is incorrectly or incompletely entered in FIGS. 11A or 11B according to an example embodiment of the invention.

FIGS. 16A through 16G are screen shots illustrating web page interfaces providing various reports and clinical outcome data according to an example embodiment of the invention.

DETAILED DESCRIPTION OF THE PREFERRED EMBODIMENTS

Figure 1:
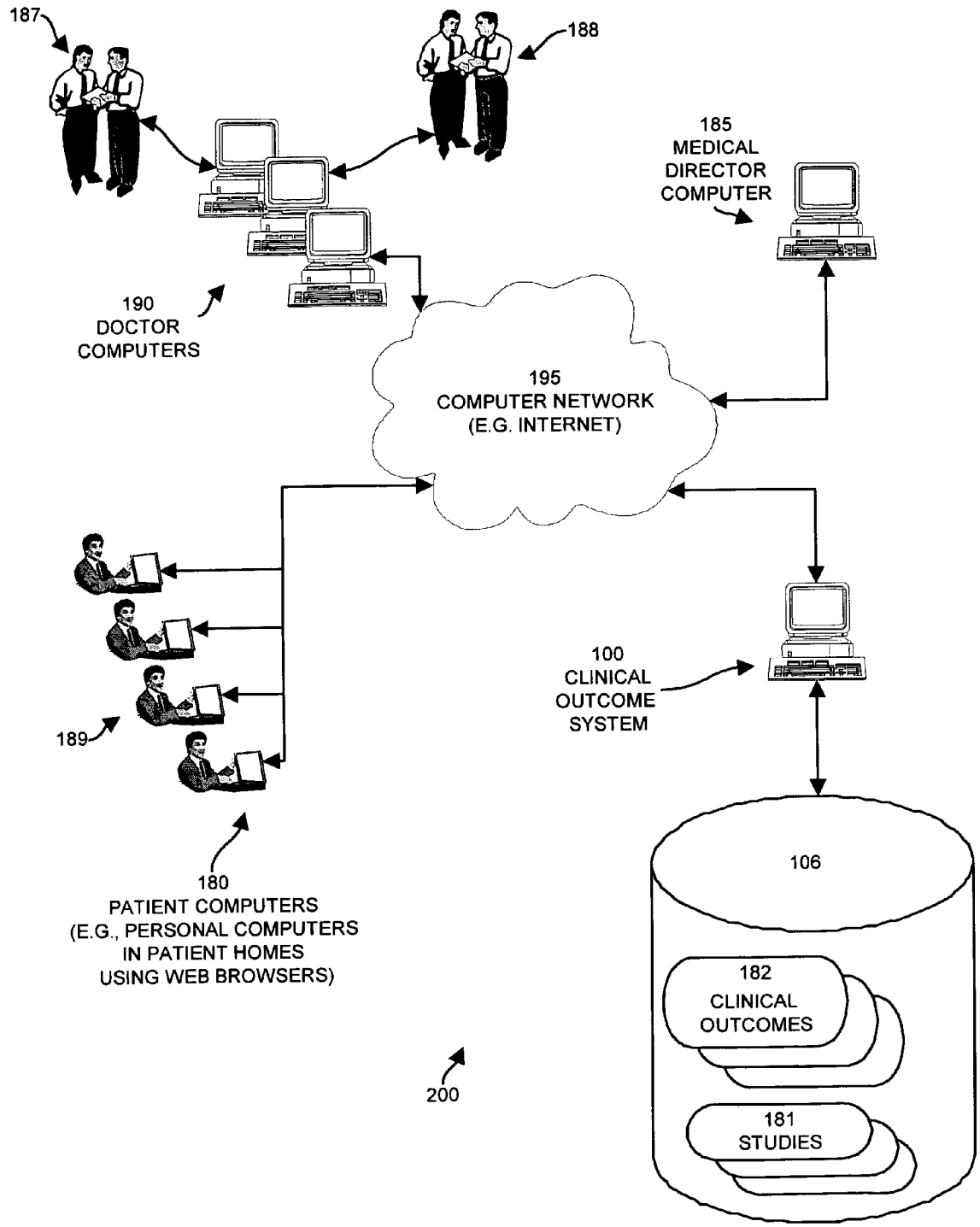
FIG. 1 illustrates a computer network including a clinical outcome digital data processing system as configured according to one embodiment of the invention.

The present invention is directed to techniques providing a tool for the assistance and administration of medical research. FIG. 1 illustrates an example of a computer networking environment 200 configured to support operation of one embodiment of the invention. The computer networking environment 200, in this example, includes a computer network 195 which interconnects one or more doctor computers 190, one or more patient computers 180, a medical director computer 185, and a clinical outcome system 100 which includes a medical database 106 configured in accordance with the invention. A brief overview of the system of the invention and its operation will assist in understanding the discussion of more detailed embodiments presented later.

Generally, as illustrated in FIG. 1, the environment 200 allows doctors and other medical professionals to efficiently carry out medical outcome research according to techniques of the invention. In operation of the system 200, doctors (or other medical professionals or medical researchers) 187, 188 access doctor computers 190 which interface over the computer network 195 with the clinical outcome system 100. Client web browser software (not specifically shown) executing on the doctor computers 190 provides the preferred mechanism for accessing data on the clinical outcome system 100. The clinical outcome system 100 allows the doctors 187, 188 at the doctor computers 190 and patients 189 at patient computers 180 to enter and access patient and medical studies 181 and clinical outcome information 182 maintained within medical databases (i.e., on disks) 106.

As a specific example, the clinical outcome system 100 allows research doctor(s) 187 to define a new medical study 181 designed to research and track treatment, in real-time, for a particular illness (e.g., breast cancer). The medical study 181, as defined, may include sets of questions (not specifically shown in this figure) for gathering medical information from treating doctors 188 and patients 189 who are to partake in research related to the medical study 181. The medical database 106 stores the medical study 181 and related information (i.e., clinical outcomes 182) once defined and entered into the clinical outcome system 100.

Treating doctors 188 can access the clinical outcome system 100 over the network 195 via doctor computers 190. The various doctor computers 190 may be located in geographically diverse locations than the doctors 187 and the specific doctor computer 190 used to define the study. The treating doctors 188, who may be located throughout the United States, for example, may register to partake in the study 181 if they happen to be treating a patient 189 that has the particular illness for which the study 181 is designed to research. At various times that the treating doctors 188 treat the patients 189 having the illness, the treating doctors 188 can use their doctor computer 190 to interface with the clinical outcome system 100 for real-time assistance in treatment by using the study 181.

When accessing the clinical outcome system 100, the clinical outcome system 100 presents the treating doctors 188 with a list of studies with which they, as participating doctors, are involved. A treating doctor 188 can then select the specific study 181 (i.e., breast cancer study) and patient data (not specifically shown) within that study 181 for the patient 189 to which treatment is about to be administered. The clinical outcome system 100 can then present a series of study questions to the treating doctor 188 at his or her doctor computer 190. The study questions presented to the doctor computer 190 may depend upon what phase of treatment the particular patient 189 is in for the overall course or protocol of treatment for the particular illness, as defined in the study 181. In other words, at each phase of treatment for patient 189, the study 181 may have particular questions to present to the treating doctor 188 just prior to a treatment.

Hence, just before treatment is administered, the treating doctor 188 can use his or her doctor computer 190 to answer the questions in the study 181 as presented by the clinical outcome system 100. The clinical outcome system 100 can then process the answers to the questions in real-time, and can execute specific clinical algorithms (not shown in this figure) that are related to the study 181 to produce one or more clinical outcome(s) 182 which are stored in the medical database 106. The answers to the questions are maintained as part of the study 181. The clinical outcome system 100 can then present the clinical outcome(s) 182 produced as a result of the doctor 188 providing answers to study questions to the treating doctor's 188 doctor computer 190. Based on the results defined in the clinical outcome 182, which take into account the most up-to-date study data gathered from potentially all patients and doctors partaking in the study 181, the treating doctor 188 might alter treatment of the particular patient 189 who is about to undergo the next phase of the protocol or treatment for the illness.

In this manner, the clinical outcome system 100 provides a mechanism to carry out a medical study 181 and also offers the ability to use the most up-to-date results of the study in real-time to effect treatment at that moment of a particular patient. By real-time, what is meant is that the clinical outcome 182 that is generated can contain the most up-to-date results which have taken into account the answers provided by the treating doctor 188 who is seeking the clinical outcome at that moment, as well as answers to questions provided by other treating doctors and/or patients provided at the same time, or any time prior to the current time.

As an example related to the above scenario, suppose that the patient 189 was entering a phase of breast cancer treatment that provided an option of obtaining a very new form of radiology treatment. Further suppose that the study 181 has been recently defined, edited, created, or modified to take into account the side effects, techniques, benefits, and so forth of the new radiology treatment. Just prior to treatment, the treating doctor 188 can answer questions related to the patient and patient care at the current phase of treatment. An example would be to provide information to the clinical outcome system 100 indicating what drug treatment has been administered and what the current state of the patient's well-being is now, just prior to treatment. Based on the answers to the questions, the doctor 188 (and the patient 189 in attendance at the doctors office or hospital) can obtain clinical outcome data 182 that provides up-to-the minute nationwide statistics concerning the effects, results, and other characteristics of the new form of radiology treatment and can provide a statistical recommendation and risk stratification, based on the answers to the study questions for patient 189, as compared to all other study questions and data provided by other patients 189 and doctors 187, 188 around the country up to the moment of processing the clinical algorithm in the clinical outcome system 100. This information, provided in "real-time" in response to the treating doctor 188 answering the study questions, can be used by both the doctor 188 and the patient 189 when making a decision to proceed or not with the radiology treatment.

Also as illustrated in FIG. 1, a patient 189 may use a patient computer 180 to interact with the clinical outcome system 100. The clinical outcome system 100 may have predefined questions in a study 181 that are specifically designed to be answered, for example, on a periodic basis by the patient 180. The patient computer 180 may be a home-based or personal computer located at the patient's 189 residence. This allows the patient to contribute to the database 106 containing study information without having to leave the house. This can be particularly useful in the administration of drug protocol studies, for example, where a patient 189 must frequently report his or her state of well-being and other information in order for the study 181 to be properly administered and carried-out.

By providing the ability for a patient 189 to enter data to the clinical outcome system 100, the invention can also provide clinical outcome data 182 back to the patient, in real-time based upon the data entered, to provide an indication of the patients 189 ranking or aggregate score, based on other patients in the study 181 at the same phase of treatment. For example, based upon the patient data entered, the clinical outcome system 100 may provide a patient 189 with clinical outcome data 182 that indicates he or she is in the top eighty-five percent as an aggregate score based upon the answers to the questions presented to the clinical outcome system 100 for the study 181. In other words, the patient 189 can be provided with rather instantaneous feedback of how that patient compares to others having a similar illness or undergoing similar treatment. This can have a reassuring effect on the patient and avoids requiring the patient to have to wait for days or weeks while the patient data is clinically processed. The clinical outcome system 100 can assure the integrity of the study by providing robust error detection and patient data validation during patient (and doctor) data entry.

Due to the dynamic nature of the clinical outcome system 100 configured according to the invention, medical databases 106 related to ongoing studies 181 are continually evolving with the most up-to-date and detailed data. In other words, the medical database 106 is prospective in nature and can be constantly collecting sets of medical information related to various studies, patients, and research in a structured manner to provide the most up-to-date and accurate clinical outcomes 182. The data is collected at a fine level of granularity thus allowing details analysis to produce a broad variety of clinical outcomes.

Also as illustrated in FIG. 1, a medical director computer 185 can interface with the clinical outcome system 100 to obtain particular clinical outcome data 182. In this instance, the medical director computer 185 may be used, for example, by a sponsor of an illness study (e.g., a drug company researching drugs to cure a particular illness), to obtain privileged clinical outcome data 182 that indicates how effective a particular doctor or group of doctors 187, 188 are at treating the illness under consideration. The clinical data 182 sent to the medical director computer 185 may be unavailable to patients 189 and doctors 187 and 188 (at computers 180, 190), based upon access control and security mechanism provided by the system of the invention. This feature of the invention allows, for instance, an HMO to commission and establish a study 182 to rank doctors 187, 188 or physicians groups (i.e., groups of doctors) on recovery rates of patients 189, as compared to other doctors and other physicians groups. Based on questions required to be answered in the study 182, and on responses from doctors 187, 188, patients 189, and possibly other entities not shown in the figure, such as hospitals, up to the minute costs can be assessed for a particular medical treatment. This aspect of the invention may be used to cross check invoices for medical care, for example, submitted by a doctor 187 or from a physicians group, or from a patient 189. Also, by providing restricted information, the integrity and privacy rights of a patient 189 may be maintained, while still allowing the patient 189 to partake in the study 182.

Another important aspect of the system of the invention, as conveyed by the illustration in FIG. 1, is that study data 182 may be used to determine clinical outcomes 182 that are not possible with prior art systems since study data 182 is collected at the patient level. This allows the system of the invention to provide cross-correlations of various detailed characteristics of sets of medical study 182 data at a very fine level granularity and detail.

By way of example, when a particular patient 189 and doctor 187, 188 are enrolled to partake in a particular study, large amounts of detailed information can be initially incorporated into a study 182 within medical database 106 for each doctor 187, 188 and patient 189. Each doctor 187 can enter information such as the doctors geographical practice location, specialty, age, education, past treatments performed, past recovery rates, and so forth into the clinical outcome system 100. Likewise, patients 189 enrolled in the study can initially enter information such as age, race, height, weight, build, past medical history, current symptoms, allergic reactions, ages and medical characteristics of parents and relatives, current medications, living conditions, occupation, salary, siblings and so forth. Since each patient is able to enter this information on their own, with little or sometimes no assistance from a doctor 187, 188 or other medical professional, time and money are saved in data entry operations. This data may only need to entered once, at the inception of the study or during enrollment of a new patient or doctor.

The patient information may be validated upon entry, and can be cross checked against data that may have been entered, for example, by that same patient 189 in a former study. Once the initial bulk study data 181 has been entered for a patient 189, during the course of the study, the clinical outcome system 100 can allow obscure queries, via customized clinical outcome algorithms (not shown in this figure), that can determine effects and outcome 182 that would have been otherwise difficult or impossible to detect or determine using prior art study administration techniques. This is due to the data being collected, even for very large studies, on a patient by patient and doctor by doctor basis.

For example, if a general clinical outcome 182 indicates a high risk of cancer for a larger than normal population of young children. The clinical outcome system 100 allows a more customized clinical algorithm to be quickly developed to gather clinical outcome data 182 related to each cancer patient under the age of fifteen, and may break the results down by geographical location. Further clinical algorithm analysis may determine other statistically common attributes between those children. As a result, patterns of cancer may be detected based upon, for example, certain traits of a child having a specific geographical location, and whose parents also had a similar type of cancer. Each time a child cancer patient 189 undergoes the next phase of treatment in the study 181, the system 100 of the invention can be consulted to determine risk strata, treatment performance rankings, composite outcomes, and many other types of information, which are all computed based on up-to-the moment study data.

The results provided by the invention are not possible with prior art systems since conventional study administration techniques do not collect the same level of detailed data at the patient level, but rather, gather data as related to groups or a populaces of patients or gather limited sets of information. Moreover, since prior art study methodologies are not real-time in nature, and cannot evolve as patient treatments and recovery statistics evolve during the study, prior art study techniques are less reliable and the results can quickly become out-of-date. The results might even be out of date at the time they are computed, due to the non-real-time nature of prior art study administration techniques.

Aside from the dynamic nature of the clinical outcome data 182 provided by the invention, the clinical outcome system 100 configured according to the invention provides pro-active treatment capabilities in many medical situations. Specifically, as illustrated in FIG. 1, if a patient 189 or a treating doctor 188, during the course of study data entry (i.e., answering study questions at any phase of a study), enters information that is of concern or is of an urgent nature, the clinical outcome system 100 can causes a trigger event to occur. Essentially, a trigger event, as its name implies, allows the system of the invention to notify, for example, a medical professional that action is required based on study data that is entered. As an example, if during the course of required monthly data entry, a patient 189, who is recovering from a cancer treatment, enters data that does not conform to a standardized or accepted level of recovery associated with the current phase of the study for the cancer treatment, the clinical outcome system 100 can send an email notification to the treating doctor 188 for that patient 189. The email may indicate to the treating doctor 188 that the patient 189 is not recovering according to the accepted level of progress. As such, the treating doctor 188 can then contact the patient 189 to determine the cause of the non-conforming recovery. Trigger events, as will be explained in more detail, can also be established for simply failing to enter data during a certain predetermined window of time during which the clinical outcome system 100 expects data to be entered for a patient 189 or doctor 187, 188 for a study 181.

As indicated in the above examples, the clinical outcome system 100 configured according to the invention allows medical studies to be efficiently carried out. Moreover, the implementation of the system of the invention provides significant advantages not found in prior art systems. Now, a more detailed discussion of certain components and techniques provided by the invention will be provided.

Figure 2:
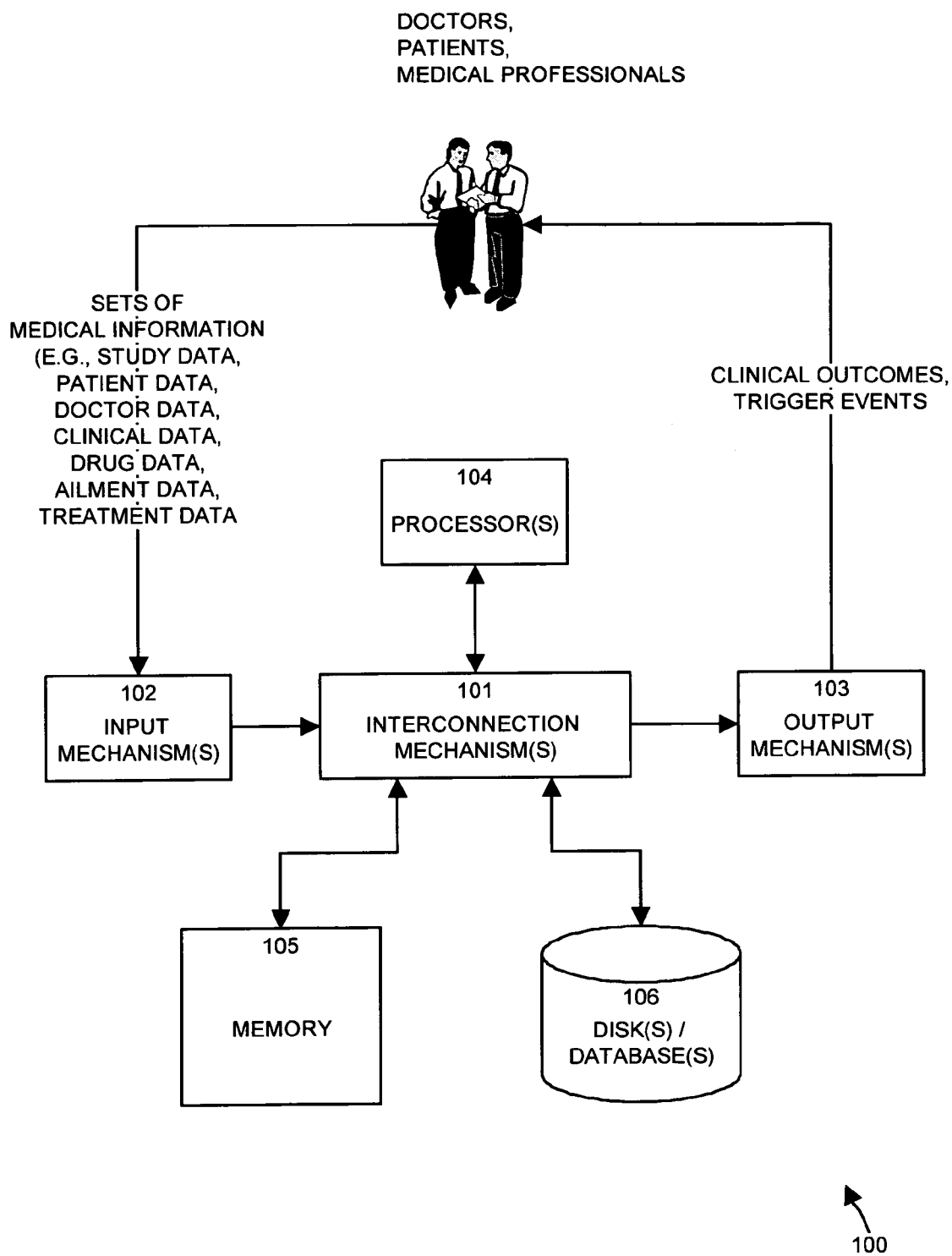
FIG. 2 illustrates a more detailed configuration of a data processing system configured according to one embodiment of the invention.

FIG. 2 illustrates a more detailed architecture of the clinical outcome system 100 configured as a digital data processing system according to the invention. The clinical outcome system 100 is generally a general purpose computer or digital data processing system which includes an interconnection mechanism 101 which couples an input mechanism 102, an output mechanism 103, a processor 104, a memory 105, and disks 106 which store medical databases (referred to herein generally as medical databases 106) as provided by the invention. A preferred embodiment of the clinical outcome system 100 is a high-powered workstation coupled via a high speed connection to a computer network (e.g., 195 in FIG. 1). Specific examples include a personal computer, Unix workstation, Microsoft Windows NT powered workstation, a cluster of workstations or computer, a mini-computer or a mainframe computer.

The input mechanism 102 may be a network connection coupled to computer network 195, or may be a keyboard, mouse or other computer input device, or may be itself a standalone computer (e.g., patient computer 180, doctor computer 190). The input mechanism 102 receives sets of medical information, which can include study data, patient data, doctor data, clinical data (answers to questions provided by doctors or medical professionals), drug data, ailment data, treatment data, and so forth. Each set of medical information generally includes characteristics related to a specific medical study and the characteristics of each set generally have an associated value.

The input mechanism transfers the sets of medical information, once received, to a storage mechanism, which in this example is the medical disk/database 106. The storage mechanism may be a file server, disk drive, database server (e.g., an Oracle database system manufactured by Oracle Corporation), web server or other data storage and retrieval system that can store all data and programs related to the invention, as well as programs, such as an operating system (not specifically shown), which allows the clinical outcome system 100 to operate.

The processor 104 is coupled, via the interconnection mechanism 101, to the disk drive 106 storage mechanism. As will be explained in more detail, the processor can process the sets of medical information (e.g., study data 182 in FIG. 1) according to characteristics by using clinical algorithms (not shown) which execute on the processor 104. The clinical algorithms produce clinical outcomes 182 for the sets of medical information (e.g., study 181) based upon the selected characteristics used by the clinical algorithms to process the sets of medical study data 181.

The output mechanism 103, which may be a network interface coupling a remote patient or doctor computer 180, 190 to the interconnection mechanism 01 and to the processor 104, receives the clinical outcomes 182 generated from processing the sets of medical study information 182. The output mechanism 103 outputs the clinical outcome data 182 to the doctor or patient users 187 through 189, thus allowing the clinical outcome data 182 to be analyzed in real-time, based on the sets of medical data 181 received by the input mechanism 102. Also output are trigger events, which were briefly discussed above and which will be discussed in more detail later.

The interconnection mechanism 101, may be, for example, a data bus within the clinical outcome computer system 100 or may be a computer network (e.g. 195 in FIG. 1), in which case each of the input and output mechanisms 102, 103 are separate computer systems (e.g., 180, 190), and in which case the processor 104 is a computer system in and of itself which processes clinical algorithms and stores the clinical outcome data 182 in a database in memory and/or disks 105, 106.

The components 101 through 106 of the clinical outcome system 100 of the invention perform the majority of the processing associated with the invention, which will be explained next. That is, the processor 104, which is a central processing unit or microprocessor, executes the steps provided by the method embodiments of the invention.

Figure 3:
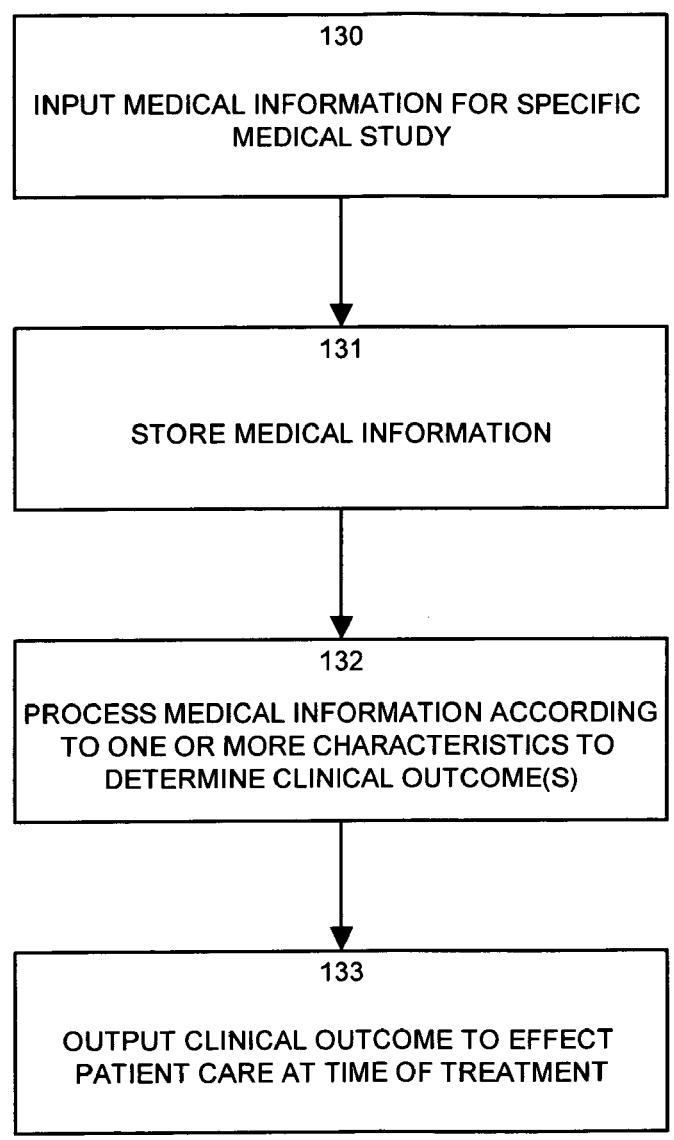
FIG. 3 is a high level flow chart of the processing steps performed to provide clinical outcomes in accordance with one embodiment of the invention.

FIG. 3 provides a high-level flow chart of the general processing steps performed according to embodiments of the invention. In step 130, the clinical outcome system 100 receives medical information as input for a specific medical study 181. The medical information, as indicated in the above examples, may be provided to initially establish the study 181, or may be doctor and/or patient data provided periodically as the study 181 progresses. It is to be understood that data for more than one medical study may be input. In step 131, the clinical outcome system 100 stores the medical information received as input in step 130. The information may be stored, for example within a centralized database maintained within disk(s) 106 that are accessible to the processor 104. In step 132, the clinical outcome system 100 processes the medical information according to one or more characteristics to determine a clinical outcome 182. A clinical algorithm designed specifically for the medical information may be used to process the medical information to produce the clinical outcome. Next, step 133 outputs the clinical outcome data which can be used to make medical determinations based upon the data input in step 130. In the example processing step 133, the clinical outcome data is used to effect a patient's case at the time of treatment and at other times during the study.

An important aspect of the invention is that the clinical algorithm can take into account medical information that was received in step 131, just prior to processing in step 132. This allows the clinical algorithm to not only generate a clinical outcome for study research purposes (which provides study results using up-to-the-moment collected data), but also allows the clinical outcome to provide the most up-to-date study information that is relevant to the person (e.g. doctor 187, 188, patient 189) entering the input in step 130. The clinical outcome system 100 also takes into account, at the time of processing a clinical algorithm, other medical information that may have been input minutes, hours, or only days beforehand from other patients, doctors, medical practitioners, and so forth. According to this aspect of the invention, the medical information used by the clinical algorithm may also be obtained from very diverse geographical locations, and thus avoids prior art problems associated with having to physically ship medical information to a central location for manual processing after treatment has already been undertaken. Since the processing is done in real-time, the treatment of a patient, as in this example, can take into account clinical outcome results from step 132. This aspect of the system of the invention was demonstrated in the former example with respect to FIG. 1, when data reported to a doctor 188 and patient 189 from processing a clinical algorithm provided the patients aggregate performance (i.e., level of treatment or recovery) as compared to that of the entire group of participants in the study, or some part thereof. It is particularly valuable that the user (e.g., doctor and/or patient) can see his or her own aggregate data against that of the entire group of study participants (or a subset thereof). This allows, for example, the doctor 188 to compare his practice in treating a specific ailment to a preset subset of other doctors that have similar practices.

Since the most up-to-date data is used for processing in step 132, and the doctor is provided with direct access to the system, there is no need for the doctor to manually request a researching organization to put together a particular clinical outcome based upon manually collected data. In other words, the doctors and/or patients themselves, through the proper selection of clinical algorithms, can put together or produce a particular clinical outcome data set in which they are interested. There can be preset clinical algorithms that can be selected to generate specific reports for such things as: a percentage of patients enrolled in a study by location; or a doctor/physician practice group versus the entire study group; a composite outcome index which can be derived by a condition-specific algorithm; comorbidity strata by user or user (e.g., patient) satisfaction data; case rates or medical costs adjusted by comorbidities for the specific ailment or condition; comparisons of composite outcomes versus treatment protocols or clinical pathways; and so on. It is to be understood that the system of the invention is not limited to such preset clinical algorithms, and that any particular study which is administered by the clinical outcome system 100 can allow customized clinical algorithms to be developed based on medical information that is to be collected during the study.

Figure 4:
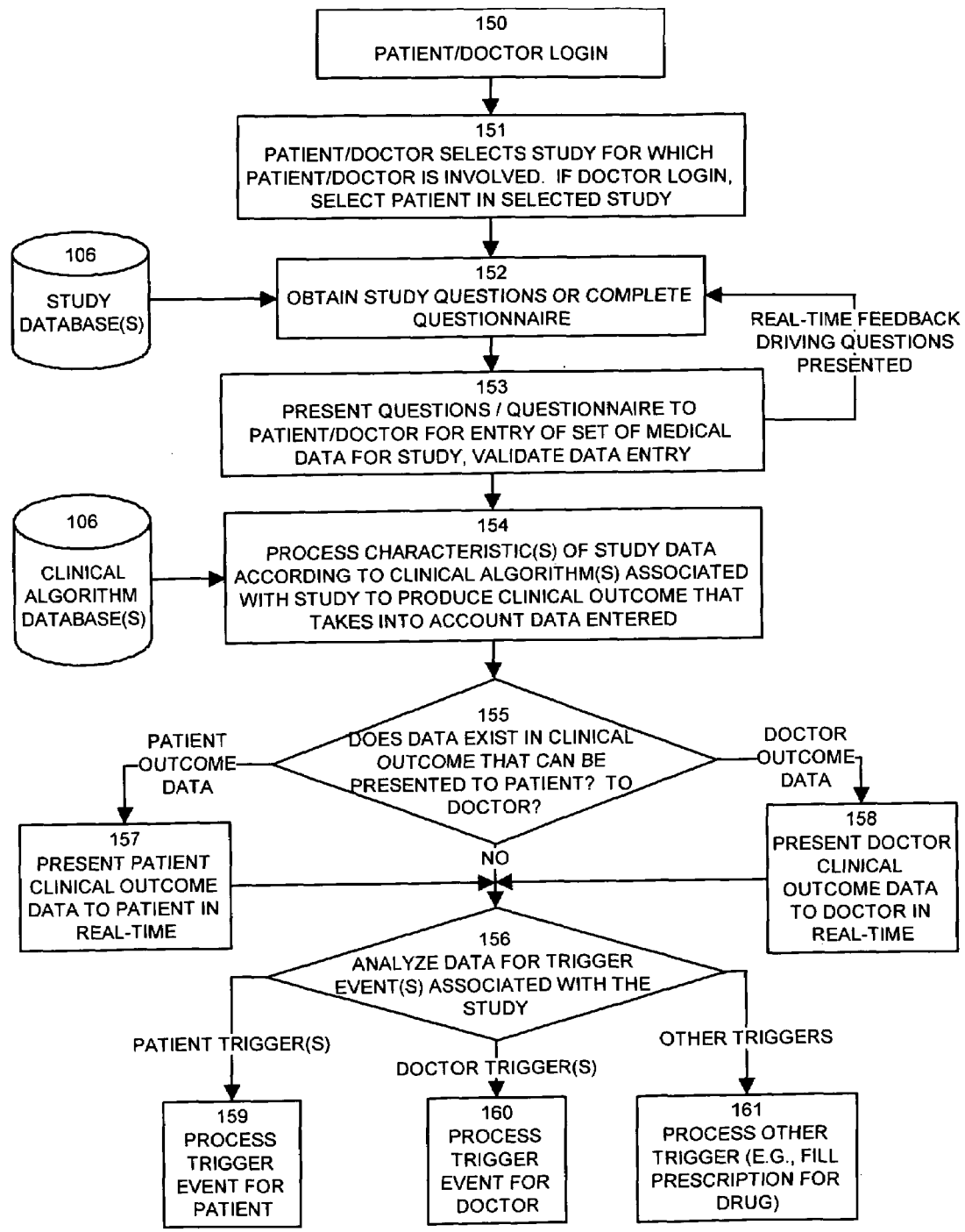
FIG. 4 is a flow chart which shows the processing steps performed to gather and process data to provide clinical outcomes according to one embodiment of the invention.

FIG. 4 illustrates a more detailed flow chart of processing steps 150 through 161 performed by the clinical outcome system 100 to allow a patient 189 (and/or a doctor 187, 188, as will be explained) to enter answers to medical study information (enter sets of medical information) for the determination of clinical outcome data according to one embodiment of the invention. In step 150, a patient 189 logs-in to the clinical outcome system 100. The clinical outcome system 100 provides access control functions, user authentication and security in step 150 to correctly identify the individual connecting or logging-in to the clinical outcome system 100.

In step 151, based on the identity of the person logging-in, the clinical outcome system 100 presents a list of available studies 181 (FIG. 1) to select and the patient 189 (or doctor 187, 199) can select a study for which the patient 189 or doctor 188 is involved. If a doctor 187, 188 is identified as the individual using the clinical outcome system 100 in step 151, then the doctor is presented with a list of studies, and once a particular study is selected, the doctor 187, 188 can then select a patient from a list of patients which that doctor is treating in relation to the selected study.

In step 152, once the clinical outcome system 100 has determined a study 181 and patient 189 associated with the study 181, the clinical outcome system 100 obtains study questions or a complete study questionnaire from the study database(s) 106. The particular questions obtained by the clinical outcome system 100 in step 152 may depend upon what phase of the study the patient 189 is currently in. In step 153, the clinical outcome system 100 presents the questions or the questionnaire to the patient 189 or doctor 187, 188, in order to obtain a set of medical information in the form of answers to the questions related to the particular phase of the study 181. Note that the answers provided by the patient 189 or doctor 187, 188 to certain questions may provide real-time feedback to drive questions presented to the user thereafter. In other words, steps 152 and 153 can be inter-related in such a way that allows the clinical outcome system 100 to determine from a response or responses to a question or questions what the next question or group of questions will be that are presented to the user of the clinical outcome system 100.

Note that in step 152 and 153, the clinical outcome system 100 incorporates robust data entry validation techniques that help ensure that the sets of medical information that are entered are accurate.

Once all of the questions have been properly answered, in step 154 the clinical outcome system 100 processes one or more specific characteristics of the study data according to one or more clinical algorithms associated with the study 181 to produce one or more clinical outcomes (e.g. 182 in FIG. 1) that take into account the data entered in steps 152 and 153. The clinical outcome system 100 may obtain the clinical algorithms from a clinical algorithm database, which may be stored along with other medical information in disks 106. More details of processing related to the clinical algorithms database and the clinical algorithms and outcomes will be explained later with respect to FIGS. 6 and 7. As previously noted, the clinical outcomes 182 can take into account the most up-to-date data entered by the current user (e.g. doctor or patient) as well as data entered by other users participating in the study 181.

In step 155, the clinical outcome system 100 determines if data exists in the clinical outcome 182 (produced as a result of step 154) that can be presented to a doctor or other medical professional 187 (doctor outcome data), 188 or to the patient 189 (patient outcome data). The clinical outcome data 182 may contain certain data that should only be presented to a doctor 187, 188, and other data that might be suitable for viewing by a patient 189.

By way of example, if a patient answers the questions in steps 152 and 153, and the clinical algorithm executed in step 154 determines that the patient is in need of medical treatment (based on responses to questions in steps 152, 153), then this information might not be suitable to be presented to the patient 189, for concern of causing unreasonable fear. As such, data of this sort can be filtered by step 155 and presented only to a doctor 187, 188 in step 158. Alternatively, if a patient 189 is required to routinely (i.e., daily) answer questions in step 152 and 153 (from a patient's home computer 180) as required by a drug study being administered by the clinical outcome system 100, the clinical algorithm processed in step 154 may frequently determine that the patient answers provided in step 153 conform to normal or standard answers. As such, the clinical outcome system 100 may detect clinical outcome data 182 in step 155 that indicates to the patient 189 that they are "on-track" for the current phase of treatment in the drug study. In step 157, the clinical outcome system 100 can send this data to the patient's 189 home computer 180.

In step 156, the clinical outcome system 100 can analyze the clinical outcome data 182 for triggering events that may be associated with the study 181. A trigger event, as explained in the former examples, is an event that may require immediate attention by either the patient 189 or a doctor 187, 188 or other medical professional, and is produced as a result of analysis of the clinical outcome data 182.

For example, if a patient responds to questions in steps 152 and 153 concerning a particular phase of a drug study, and the set of medical information gathered from that patient is analyzed and processed by a clinical algorithm in step 154, the clinical algorithm may determine or may provide an indication in the clinical outcome data 182 that the patient requires a second drug to offset a reaction being sustained by the patient 189. The reaction can be determined to be taking place by the clinical algorithm based on the patient's 189 responses to the study questions in steps 152, 153. As such, the clinical outcome data 182 may signal a trigger event for the patient's treating doctor 188 to write a prescription to offset the side effect of the drug under study. The doctor trigger event detected based on clinical outcome data 182 and then as generated in step 155 is then processed by the clinical outcome system 100 in step 160. The trigger event may for example, cause the clinical outcome system 100 to send the treating doctor 188 an email notification indicating a specific drug to be prescribed to a specific patient 189. The treating doctor 189 can then call the patient 189 to confirm the diagnosis and can issue the prescription for the counteracting drug specified in the clinical outcome data 182 that can be used to offset the reaction sustained by the patient 189.

Patient trigger events are also provided and processed by the clinical outcome system 100 in step 159. Patient trigger events may cause the clinical outcome system 100 to provide an indication to a patient 189 (e.g., via email) to call their treating doctor to schedule a visit based on the clinical algorithm analysis of the responses received in steps 153 and 153. Other trigger events can be processed by the clinical outcome system 100 in step 161. An example would be to cause the prescription in the above example to be written and sent to a pharmacy to be filled. Then, when the treating doctor 188 calls the patient 189 to confirm the patient reaction, the pharmacy will have already received and begun processing the prescription. Another example is to notify a sponsor of a study when a particular patient 189 or group of patients have successfully completed all phases of a study 181.

It is important to understand that the examples given with respect to steps 150 through 161 in FIG. 4 are merely example uses of the clinical outcome system 100 according to the invention. In a situation where the clinical outcome system 100 is used to rate the performance of doctors against other doctors or physicians groups, clinical outcomes may indicate rankings of doctors by specialty, geographical locations, treatment of particular diseases, and so forth. The trigger events in these circumstances might be related to signaling the head of a physicians group, for example, if a clinical outcome 182 of a study 181 indicates that a particular doctor 187, 188 is doing excessively poorly or exceptionally well in treating a particular ailment or patient 189. In the later case, a trigger event may be processed by the clinical outcome system 100 in step 161 that provides a compensation bonus to all doctors in a practice group that meet certain clinical outcome criteria, such as having a treatment success rate combined with a patient satisfaction rate (as determined by patient input in steps 152, 153) of over eighty percent. This information can be gained by the system of the invention in real-time, thus allowing doctor performance in areas of treatment, patient satisfaction and so forth to be gauged based on the most up-to-date data in the study 181.

Figure 5:
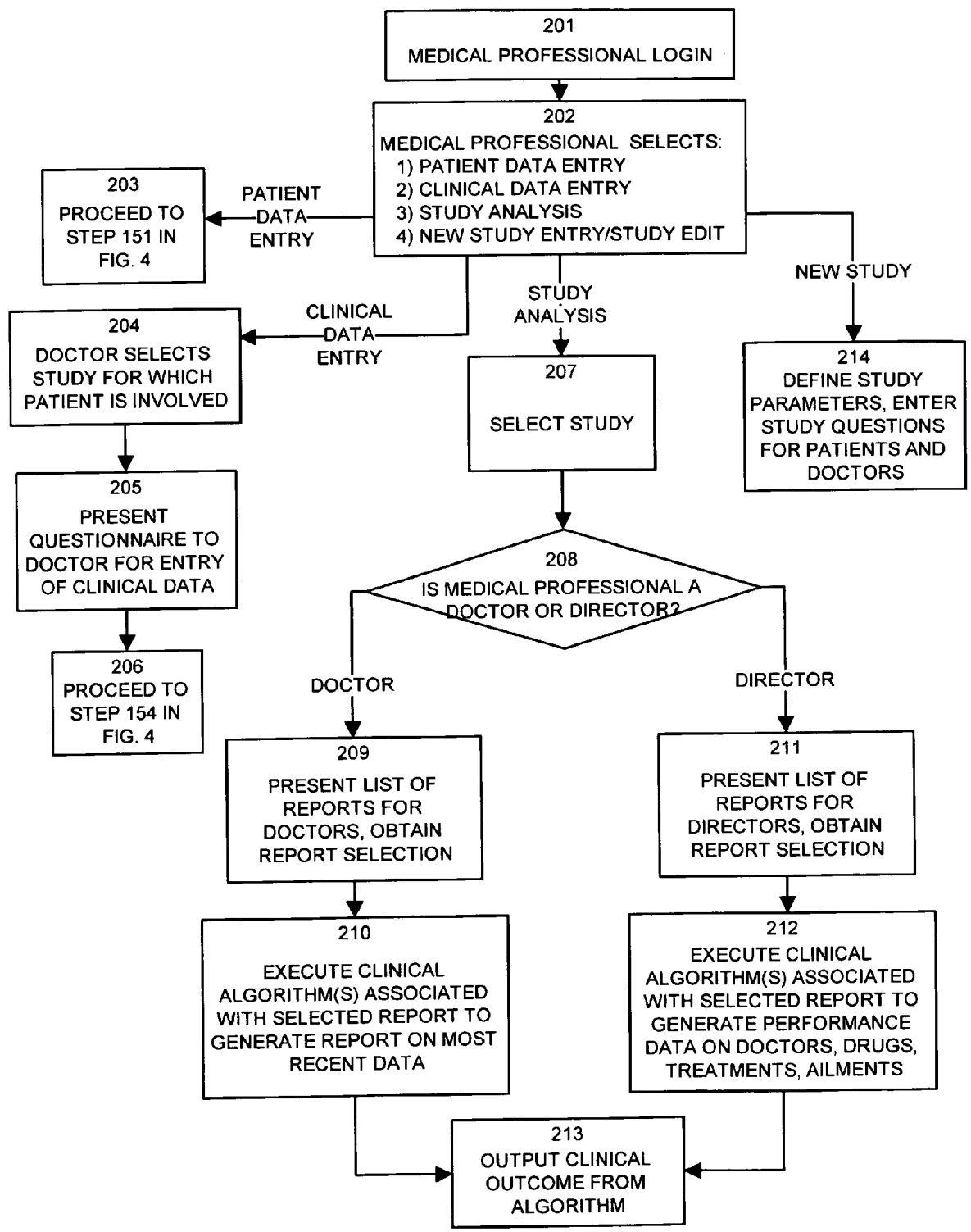
FIG. 5 is a flow chart of the processing steps provided to allow a medical professional to control the general operation of the system configured according to the invention.

FIG. 5 is a flow chart of the processing steps 201 through 213 performed by the clinical outcome system 100 which allow a medical professional such as a doctor 187, 188 or the head of a physicians practice group to interact with the clinical outcome system 100. In step 201, the medical professional (i.e., non-patient) logs into the clinical outcome system 100. Similar identity and authentication checks can be performed, as previously explained, for the person logging in to assure the integrity of the clinical outcome system 100. In this description, it is assumed that the doctor 187 is connecting (i.e. logging in) to the clinical outcome system 100.

In step 202, the clinical outcome system 100 presents a list of selectable options to the doctor 187. In this example embodiment, the options include 1) patient data entry, 2) clinical data entry, 3) study analysis and 4) new study entry/study edit. Depending upon the users (i.e. doctors) selection, the clinical outcome system 100 processing proceeds to one of steps 203, 204, 207 or 214, as indicated in the figure. If the doctor 187 selects patient data entry (e.g., a doctor entering answers on behalf of a patient being examined in the doctor's office), the clinical outcome system 100 proceeds to step 203, which directs processing to step 151 in FIG. 4, to proceed as previously explained. Thus, patient data entry performed by a doctor is essentially the same as that performed by a patient, except that, as explained above, step 151 allows the doctor to select a study, and then a patient within the study.

If in step 202, the doctor 187 selects clinical data entry, then the clinical outcome system 100 proceeds to processing in step 204. In step 204, the doctor 187 can select from a number of studies in which that doctor 187 may be involved, and can then select a patient in the study for which the doctor is currently treating. After study and patient selection, the clinical outcome system 100 proceeds to processing in step 205, where a clinical data questionnaire is presented to the doctor 187 for the particular study/patient combination. The clinical data questionnaire (not specifically shown in this figure) may contain a series of questions relating to the medical treatment provided to this patient in relation to the illness of the patient for the selected study. Thus, the clinical data questionnaire presented by the clinical outcome system 100 in step 205 to doctors 187, 188 is generally quite different than the questionnaire presented to patients 189 in step 152 of FIG. 4. The clinical data questionnaire is designed to obtain the doctor's 187 information concerning, for example, how a drug is administered, how a patient is treated, and how a particular illness or ailment is diagnosed by the doctor 187. As in steps 152 and 153 in FIG. 4, questions may be presented based upon answers obtained from former questions, thus allowing dynamic feedback to drive the sequence of questions presented to the doctor 187.

Once the clinical outcome system 100 obtains a complete set of clinical medical information for the doctor's 187 responses to the questions in step 205, processing can proceed to step 206, which directs the clinical outcome system 100 to process step 154 in FIG. 4. Thus in this embodiment, when the doctor 187 provides clinical data, step 154 can be used to execute a clinical algorithm to produce clinical outcome data 182 which takes into account the doctor's answers provided in step 205. The doctor 187 is able to select the particular clinical algorithm and/or characteristics of study data to be processed in step 154. This allows the doctor to obtained customized clinical outcome data 182 for an area of the study data that he or she may have a particular interest.

This is an important aspect of the invention. Since the study data (i.e., sets of medical information collected in steps 152, 153, 205, and, as will be explained, in step 214) is collected on a doctor-by-doctor and patient-by-patient level of granularity, the clinical outcome system 100 of the invention allows very detailed analysis of study data. Also, since the study data is maintained in a centralized database on disks 106, almost any possibly imaginable cross-correlation of data can be performed by a doctor 187 selecting or defining a clinical algorithm in step 154 that provides the desired research or study results in the form of clinical outcome data 182. The clinical outcome system 100 system can even allow cross-correlation of clinical outcome data from different studies, since the flexibility of the system is limited only by the selection of clinical algorithms, which can be customized or designed from scratch. Preferably, there are a number of standard clinical algorithms produced when the study is designed, and the doctors who use the clinical outcome system 100 routinely can select from the standard clinical algorithms to generate clinical outcome reports. Alternatively, however, the invention is not limited to the pre-defined clinical algorithms.

Returning now to the discussion of processing in step 202 in FIG. 5, if the doctor 187 selects study analysis (option 3), the clinical outcome system 100 proceeds to process step 207, which allows the doctor 187 to select a particular study to analyze. Study analysis essentially allows a doctor 187 or other medical person using the clinical outcome system 100 to generate and/or obtain, search and correlate clinical outcome data, using the clinical algorithms if needed, without having to enter clinical or patient data at that time. The level of study analysis provided to the user (doctor 187, 188, patient 189) by the clinical outcome system 100 in this embodiment is determined by the identity or access privileges of the person using the clinical outcome system 100. Thus in step 208, the clinical outcome system 100 in this embodiment determines if the medical professional who logged-in in step 201 is a doctor or a medical director. This aspect of the invention allows study results to be further filtered according to who is asking for the results. If an individual doctor is asking, then the clinical outcome system 100 can provide certain information, whereas if a medical director sponsoring the study is asking, that person may have full privileges to see study data that indicates how all doctors are performing, for example, in relation to one another.

If a doctor is requesting study analysis in step 208, then the clinical outcome system 100 processes step 209 and presents a list of reports available for this particular doctor. A report in this example may simply be a name given to one or more clinical algorithms to be executed. In this instance, the clinical outcome system 100 executes each clinical algorithm specified in the report to generate clinical outcome data in the form of a report on the most recent study data. Alternatively, a report can be selected that may take some time to execute, and may thus be run in a batch mode. In any event, steps 209 and 210 allow a doctor to run reports and clinical algorithms on the most up-to-date study data to determine medical outcomes based upon the clinical outcome data generated as a result of executing each report (e.g., sets of clinical algorithms).

If the clinical outcome system 100 determines that a medical director is requesting study analysis in step 208, the clinical outcome system 100 executes step 211. In step 211, the clinical outcome system 100 allows the medical director to select from a list of reports or clinical algorithms designed to be executed by medical directors for study analysis. Then, in step 212, the clinical outcome system 100 executes any clinical algorithms associated with the selected report (step 211) to generate, for example, performance data on doctors, drugs, treatments or ailments. The difference between steps 211 and 212 in comparison to 209 and 210 is that a director is presented with reports that can generate privileged or sensitive information concerning a study. Information such as doctor rankings, treatment scores, compensation bonuses, treatment and doctor billing rates and costs, and so forth might be generated when the clinical outcome system 100 executes a director report. Conversely, a doctor report might generate large amounts of detailed information that may be of little interest to the medical director of a practice group. Once report data (e.g., clinical outcome data 182) is generated, the clinical outcome system 100 outputs this data from the report or clinical algorithm(s) in step 213.

The processing of steps 208 through 213 allows the system of the invention to serve multiple goals in relation to the same study. For instance, a doctor may be concerned with how his ranking compares with treatment of an illness versus other doctors, whereas the medical director might be concerned about costs associated with each particular treatment as compared with the overall performance of those doctors in relation to one another.

Returning once again to the discussion of step 202, if a medical professional (e.g., a study designer or researching doctor) desires to create a new study or to change or edit a study, option four is selected in step 202 and the clinical outcome system 100 processes step 214. In step 214, the clinical outcome system 100 allows the user to define study parameters, enter and define study questions for patients and clinical questions for doctors, define study timelines, trigger events, specify drug protocols, and so forth. This allows the clinical outcome system 100 system to be flexible and adaptable to new studies that are required, and allows old studies to be updated with new questions based on clinical outcome data 182 that can be generated during the life of the study.

As an example of this feature of the invention, if a drug protocol study is underway, and a significant number of patients report having a particular side-effect from the drug in a general comment question presented to the patient in steps 152 and 153, the study designer may run a clinical algorithm to determine how often all study patients have experienced such side-effect symptoms. If the symptom appears frequently, then the study 181 itself may be edited and a question may be added to the patient and doctor (i.e. clinical) questions list asking all patients if the side-effect is present. This goes far beyond the ability of prior art medical study administration systems, which offer no ability to dynamically alter the study once study materials (i.e., questions) are printed and distributed nationwide.

Figure 6:
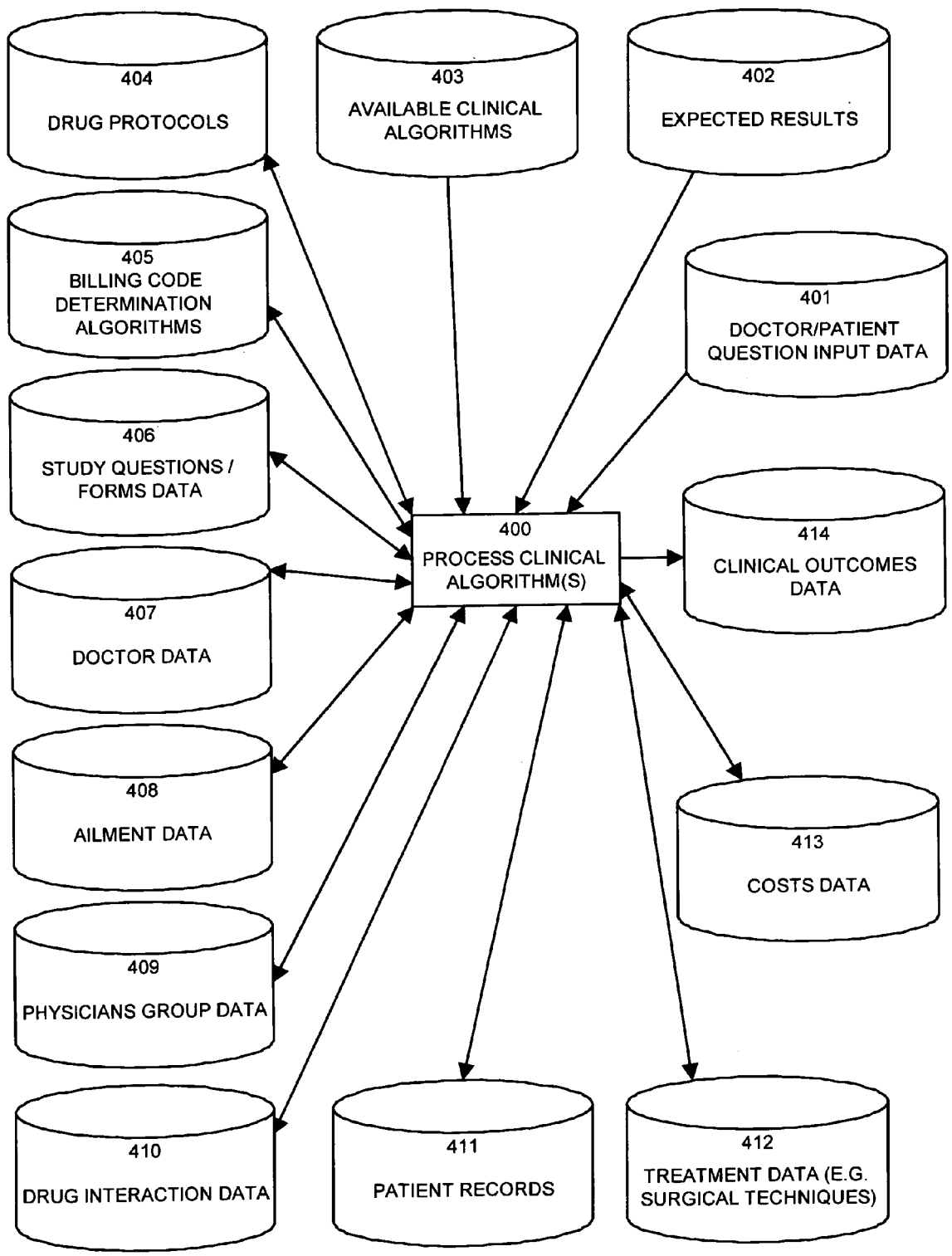
FIG. 6 is a data flow diagram indicating various example databases and data that can be taken into to account when processing a clinical algorithm to produce a clinical outcome according to embodiments of the invention.

FIG. 6 illustrates some examples of data that may be incorporated into the processing of a clinical algorithm 400 according to embodiments of this invention. In FIG. 6, the clinical algorithm 400 can access data in any one of databases 401 through 413 to produce the clinical outcomes database 414. Database 401 includes the doctor and patient answers to the questions presented in steps 152 and 153 in FIG. 4. The expected results database 401 includes standard, default or expected answers to study questions. Data in the expected results database 402 can be compared with doctor and patient answer data in database 401 to determine, for example, if a trigger event should be processed in step 156.

The available clinical algorithms database 403 can contain the clinical algorithms used by studies in the clinical outcome system 100 according to the invention. As a clinical algorithm 400 executes, it may call upon other clinical algorithms in database 403. A clinical algorithm itself, may be, for example, a simple or very sophisticated database query. Other databases 404 through 413 that can be accessed by the clinical algorithm(s) 400 include information such as drug protocols 404, billing code determination algorithms 405, study questions and forms data 406, doctor data 407, ailment or illness data 408, physician group data 409, drug interaction data 410, patient medical records data 411, treatment technique data 412, and medical cost data 413. Data from each of the databases 401 through 413 can be processed and queried by clinical algorithms 400 to produce the clinical outcomes data 414.

Figure 7:
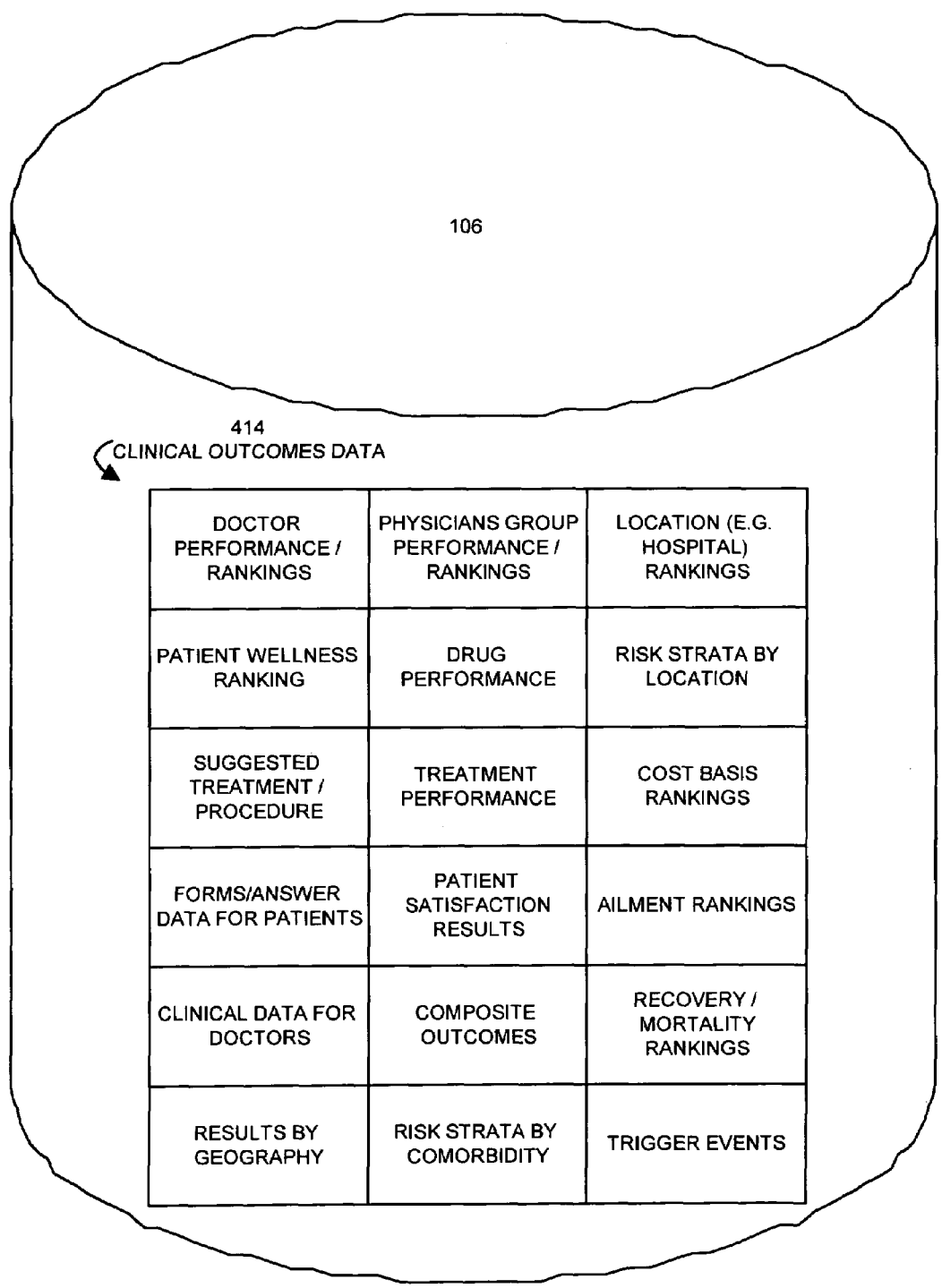
FIG. 7 is an example of a detailed view of data that can be generated in a clinical outcomes database from processing clinical outcome algorithms according to embodiments of this invention.

FIG. 7 illustrates an example of clinical outcomes data 414. As illustrated in this example, clinical outcomes data 414 can include such things as doctor and physician group performance rankings which includes rankings of doctor and/or group performance with respect to costs, effectiveness of treatments, patient satisfaction, and other factors. Also included in the clinical outcome data 414 can be such things as patient wellness rankings, suggested treatments and/or procedures for specific situations, answer information provided by doctors and patients, clinical data provided by doctors, correlation results of data analysis by geographical location, rankings of doctors and patients and physicians groups by geographical location, drug performance results, treatment performance results, composite outcomes that include cross-correlations of all or selected study characteristics, ailment rankings, costs basis rankings, recovery and mortality rankings, risk stratification such as by location, and trigger event data. It is to be understood that the data illustrated in FIG. 7 is provided as an example only. Clinical algorithms 400 may produce more or less data as required.

One important aspect of the clinical outcome system 100 configured in accordance with the invention is that the clinical outcomes data 414 is completely variable in selection and is produced based on very current sets of data and medical information. Thus, the clinical outcomes data 414 not only can be used as research results for an ongoing study, but can be used for real-time treatment or instant awareness as to the current state of study data. As explained with respect to the above example, this allows the clinical outcome system 100 to administer studies and allows doctors to carry out research in a much more organized way. Since the doctors are presented with only the study data for which they are involved, and can then be presented only with patients in those studies for which they are involved with (i.e., treating), time is saved for the doctor since his or her attention is focused on the particular subjects of interest.

FIGS. 8 through 16 shows actual screen shots taken from an example user session when interacting with a clinical outcome system 100 configured according to the invention and operating generally as previously explained in the former embodiments. The user interface to the clinical outcome system 100 as illustrated in FIGS. 8 through 16 is preferably provided by world wide web (WWW) browser software, such as Netscape Navigator, manufactured by Netscape Communications Corporation or Internet Explorer, manufactured by Microsoft Corporation. Preferably, the browser software executes on either a patient computer 180, or, as in this example on a doctors computer 190 (FIG. 1) within the doctor's 188 home or office.

Figure 8:
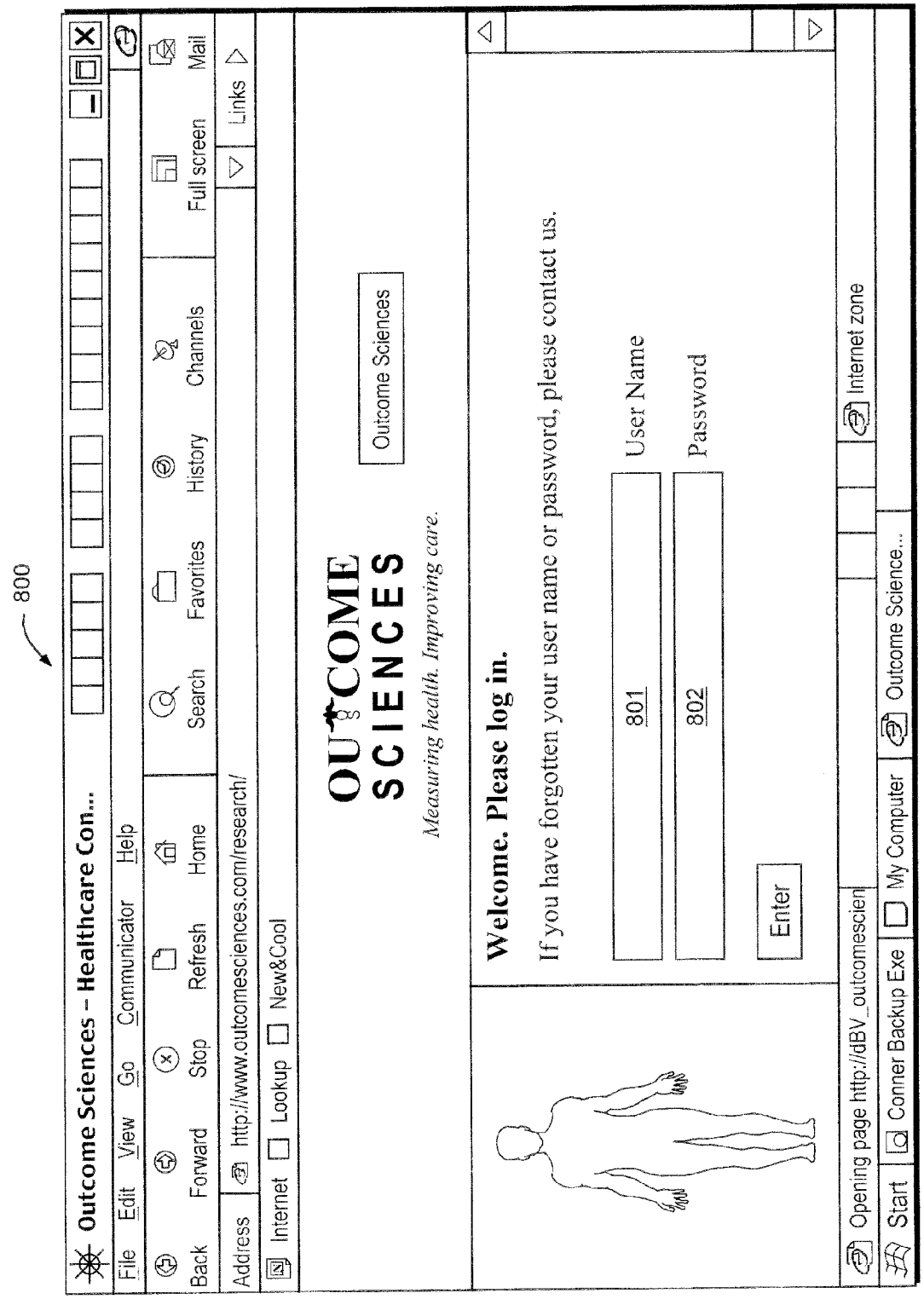
FIG. 8 is a screen shot illustrating a web page interface used to login to a clinical outcome system configured according to an example embodiment of the invention.
Figure 9:
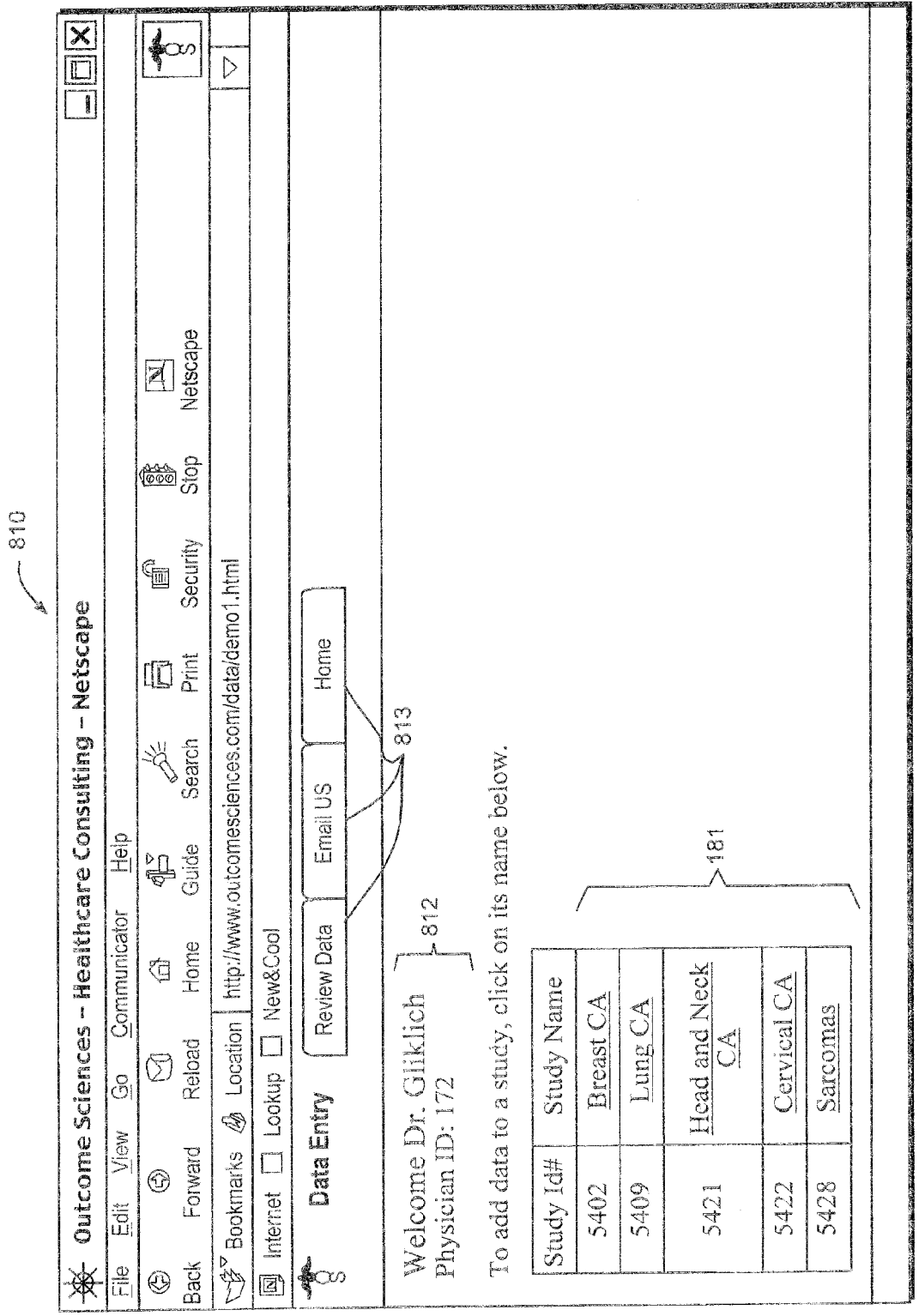
FIG. 9 is a screen shot illustrating a web page interface used to select a study for data entry according to an example embodiment of the invention.

In FIG. 8, the clinical outcome system 100 presents the user, which in this example is a doctor (e.g., 188 in FIG. 1) with a web page display 800 that allows the user to provide a username 801 and password 802 for access to the clinical outcome system 100. Once the clinical outcome system 100 verifies access for the doctor, the clinical outcome system 100 presents a screen or web page 810 as shown in FIG. 9 to the doctor 188. The web page 810 indicates each study 181 in which the doctor 188 is involved, and also provides the identity 812 of the doctor 188. Tabs 813 across the top of the web page 810 indicate various functions offered by the clinical outcome system 100. In this example scenario, the doctor is about to enter patient data for the lung cancer study number 5409 and thus the doctor 188 selects the underlined word "Lung CA," which causes the clinical outcome system 100 to present the web page 820 in FIG. 10A (or web page 825 in FIG. 10B, as will be explained) to the doctors computer 190.

In web page 820 in FIG. 10A, the clinical outcome system 100 provides a list 821 of all patients 189 (listed by patient numbers) that are involved in the study selected from screen 810. For each patient 821, various columns indicate the phase(s) 822 of treatment that each patient in currently undergoing or that they are about to enter. In this example study, there is an initial phase, and then three, six and twelve month phases 822. For each phase 822 for each patient 821, an "x" 823 indicates whether or not that patient 821 has completed that portion or phase 822 of the study. The underlined word "next" 824 indicates a link to the next uncompleted phase of data entry for the study for each patient 821. When the doctor 188 selects (i.e., using a mouse or other pointing device on the doctor computer 190) "next" 824 in FIG. 10, the clinical outcome system 100 provides the doctors computer 190 with the web page 830 shown in FIG. 11. As will be explained next, an alternative interface to web page 820 is illustrated in FIG. 16H which provides a more detailed indication of phase completion dates and study progression and remaining study requirements for a particular patient.

FIG. 10B illustrates an example of a web page interface 825 that may be used as an alternative to the web page interface 820 in FIG. 10A. Web page interface 825 in FIG. 10B may be presented from the clinical outcome system 100 to the doctor's computer 190 once a study 181 has been selected from the web page 810 in FIG. 9. Within web page interface 825, study phase data (patient name 821, phases 822A through 822D, Surg. Path. 881) is listed for each patient 821 in individual rows. In this example, study phase data is illustrated for the patients named "Chris" and "Megan." Instead of the "Initial," "3 Month," "6 Month," and "12 Month" phases 822 as presented in web page 820 in FIG. 10A, web page interface 880 in FIG. 10B presents more detailed information concerning the phases of a study as related to a particular patient 821. The titles 883 of each phase, such as "Biopsy", can be selected, which causes the clinical outcome system 100 to present a form related to treatment or procedures associated with that phase, such as biopsy treatment procedures or patient data collection, as in this example.

In this example related to a breast care study, a study information section 882 indicates such things as the name of the study, the physician ID of the doctor, and a legend 884 to be used to interpret the study phase data 822. The legend 884 includes indicators, such as "Italic text," "Regular Text," and shading for "Overdue" phases of the study. A doctor 188 can use the legend 884 to interpret the study phase data 882A through 888D, and 881, to determine the detailed study progression for each patient 821. Phase data 822A through 822D can include regular text (i.e., non italicized) or italicized labels such as "Initial," "if performed," and/or a date, instead of the simple "x" or "next" as used in the web page 820 in FIG. 10A. Since the clinical outcome system 100 can present study phase data for patients 821 in this manner, doctor(s) 187, 188 viewing the web page 825 can gain insight into each patient's 821 status as related to the study.

For example, for the patient 821 named "Chris", it is easy for a doctor 188 to determine from web page 825 that Chris's six month visit is upcoming on Nov. 11, 1999, since the date "Nov. 3, 1999" is displayed (in italics thus indicating an upcoming phase) for the "6 Month" phase 822D of the study phase data for Chris. As another example, it is easy for a doctor 188 to determine from web page 825 that the "Initial" phases 822A for patients "Chris" and "Megan" have been completed, since the clinical outcome system 100 has presented web page 880 with phase data 822A for these patients that has been shaded with a dark background and the words "Initial" for this phase 822A are indicated in regular text (i.e., not italicized). Using mechanisms such as shading, italicization, and descriptive titles, the web page interface 825 can provide very complete information for the current state of a patient's 821 progress within a study. This aspect of the system of the invention saves considerable amounts of time for a doctor 187, 188 since the doctor does not have to sort through patient study data to determine what the next course of a study is for a particular patient.

FIGS. 11A and 11B illustrates a web page 830 (split between pages due to the length of data on the web page as displayed within the web browser) that contains patient questions 831 that are to be filled out to complete the current phase of the study for the selected patient. In this example, there are fifteen questions 831 related to the physical well-being of the patient. Since the doctor logged-in in this example scenario (FIG. 8), the doctor answers the questions on behalf of the patient who may be present in the doctor's office. The answers 832 in this example are ranges from one to four and "yes" or "no" indicating a state of well-being for the patient. Once all questions 832 are complete, the doctor submits the form using the submit button 833 (FIG. 11B).

Figure 12:
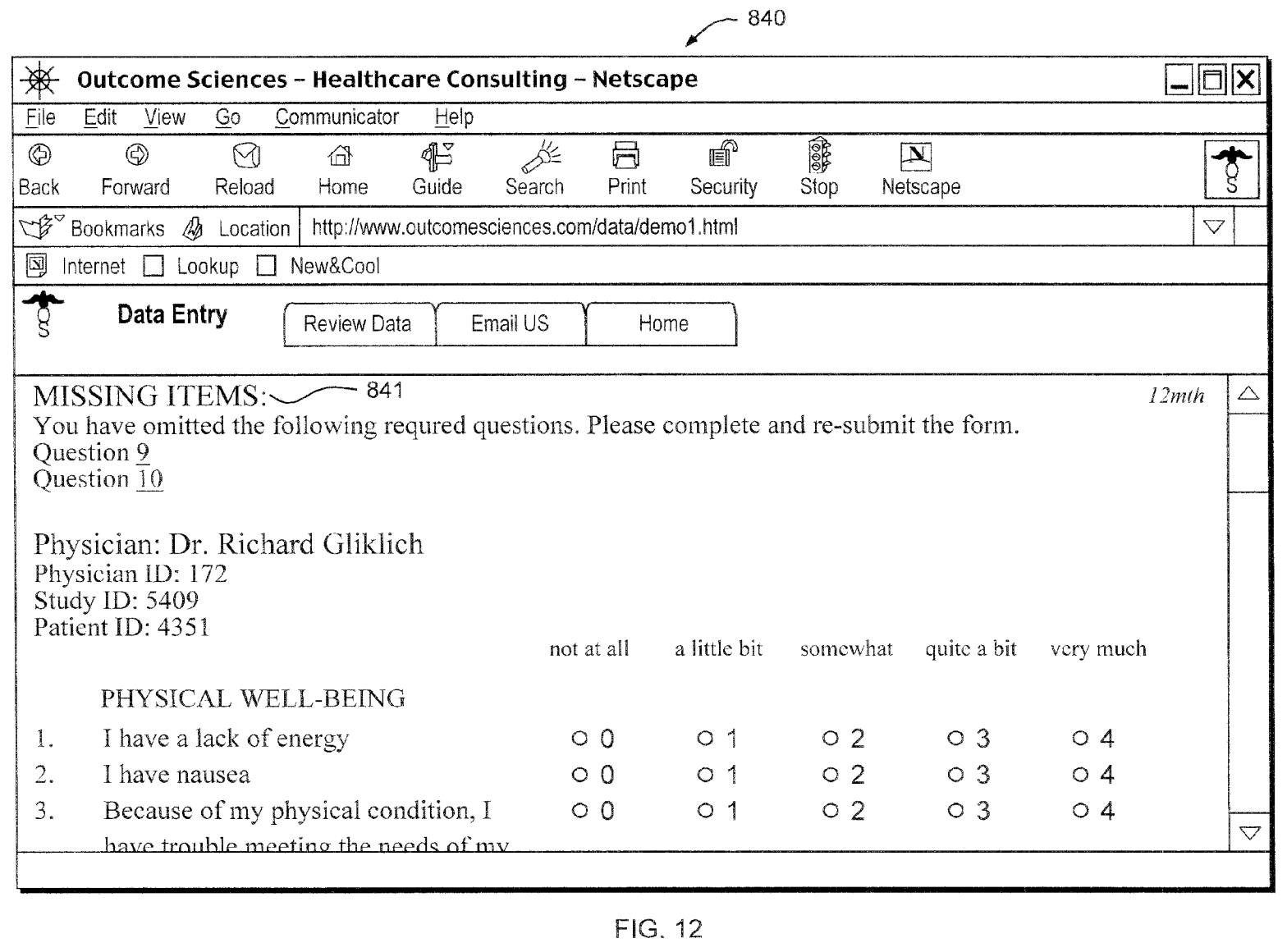

If form submission is attempted by a user before properly completing all of the questions 832, the web page 840 in FIG. 12 is provided from the clinical outcome system 100 to the doctors computer 190 and indicates 841 to the user the missing or required data. Once the form is properly completed, form submission using button 833 causes the clinical outcome system 100 to present the web page 850 in FIG. 13 which indicates that the set of medical information (answers to questions 832) for the patient has been successfully stored by the clinical outcome system 100.

Figure 13:
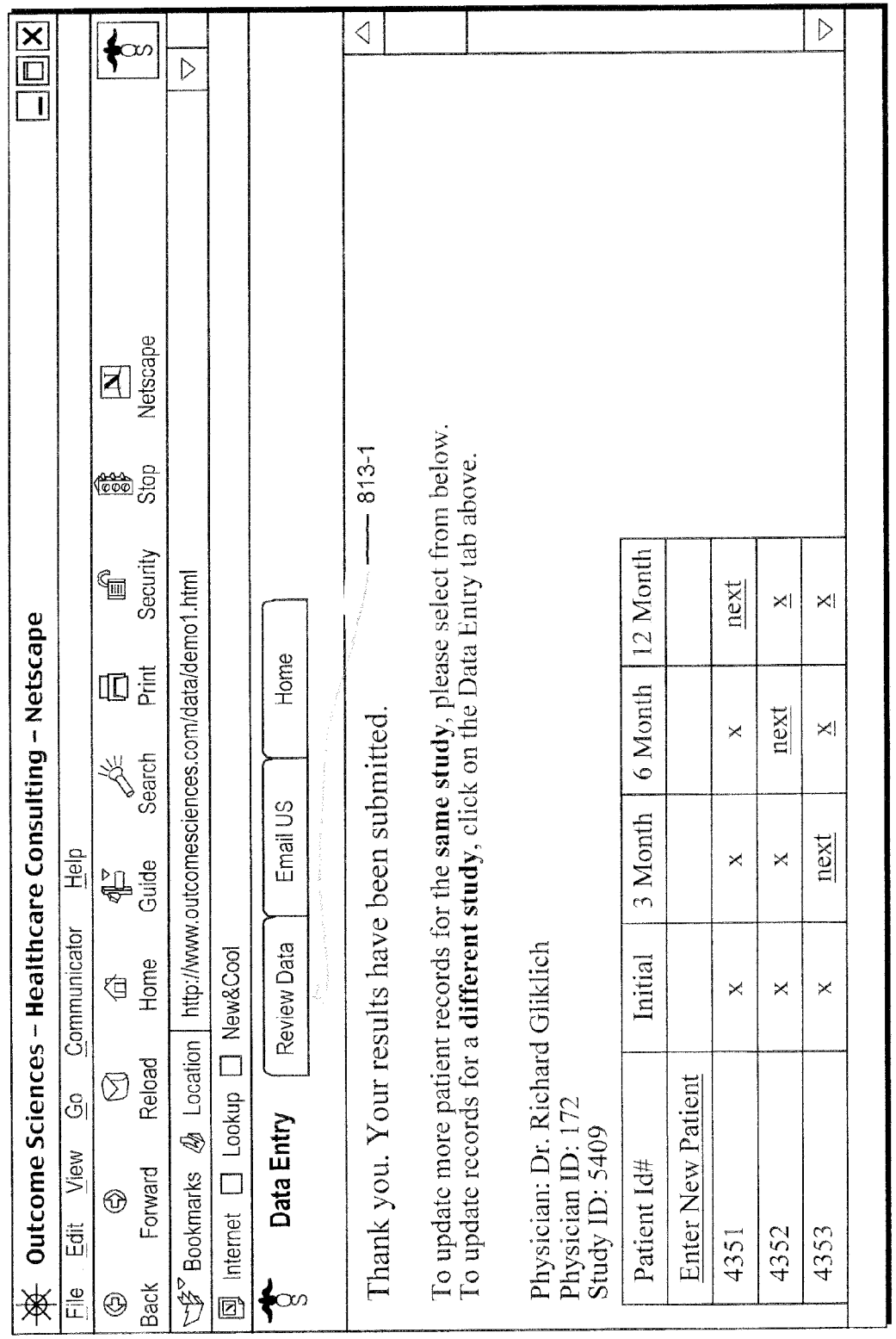
FIG. 13 is a screen shot illustrating a web page interface used begin the review data process according to an example embodiment of the invention.
Figure 14:
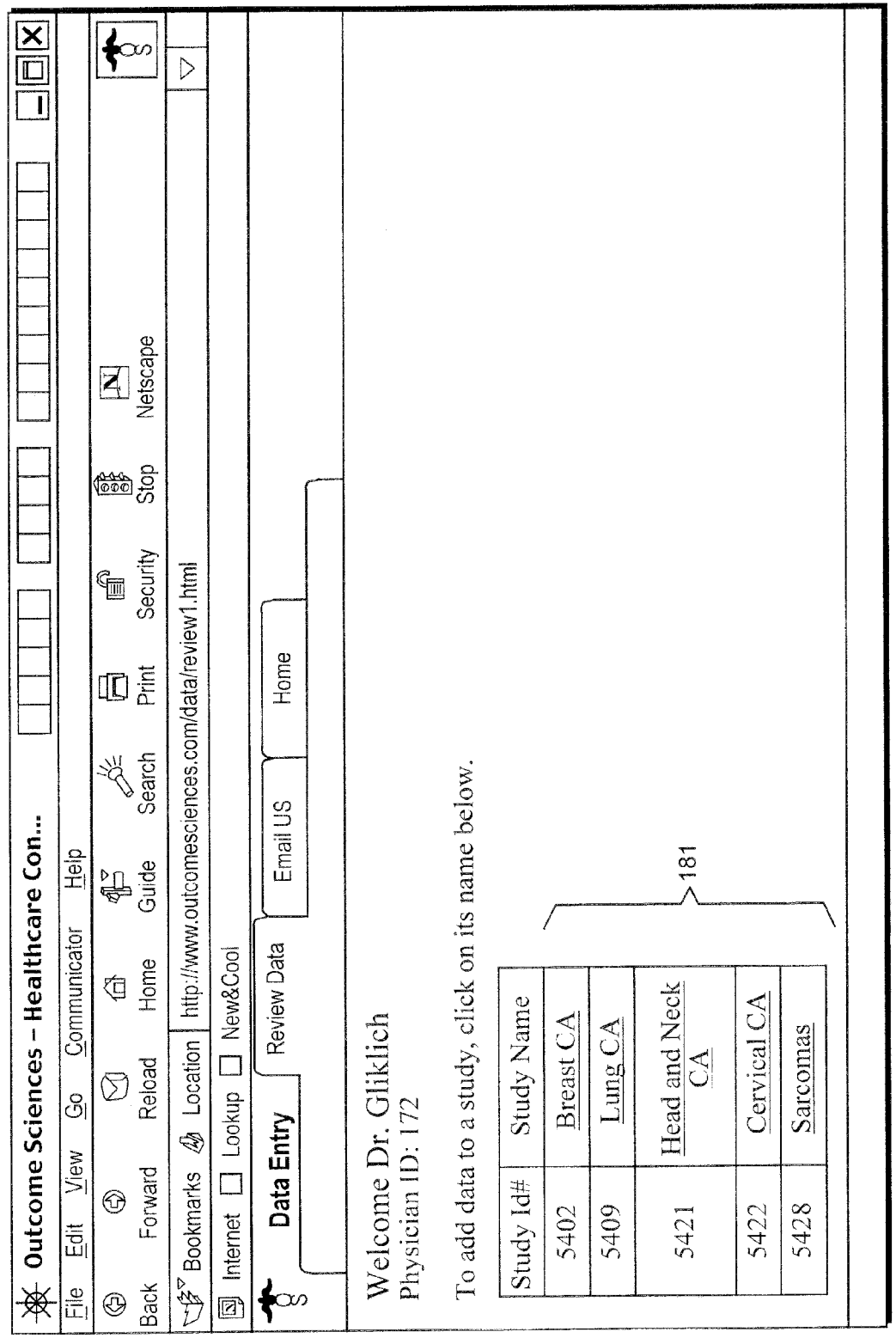
FIG. 14 is a screen shot illustrating a web page interface used to select a study for review according to an example embodiment of the invention.

By selecting the "Review Data" tab 813-1 in FIG. 13, the clinical outcome system 100 presents the web page 860 in FIG. 14. The doctor may then select one of the studies 181 to analyze clinical outcome data. In this example scenario, the doctor selects the "Lung CA" study 181, having study ID number 5409 and the clinical outcome system 100 presents the web page 870 in FIG. 15.

The results page 870 indicates a number of clinical algorithms or reports 871 that may be selected. When the doctor selects a specific clinical algorithm 871, the clinical outcome system 100 generates medical outcome data (182 in FIG. 1), in real-time, by analyzing the most current sets of medical information entered for the particular study according to the queries and instructions defined for the particular selected clinical algorithm 871. In this example, the data entered for questions 832 is taken into account during this analysis.

Figure 15:
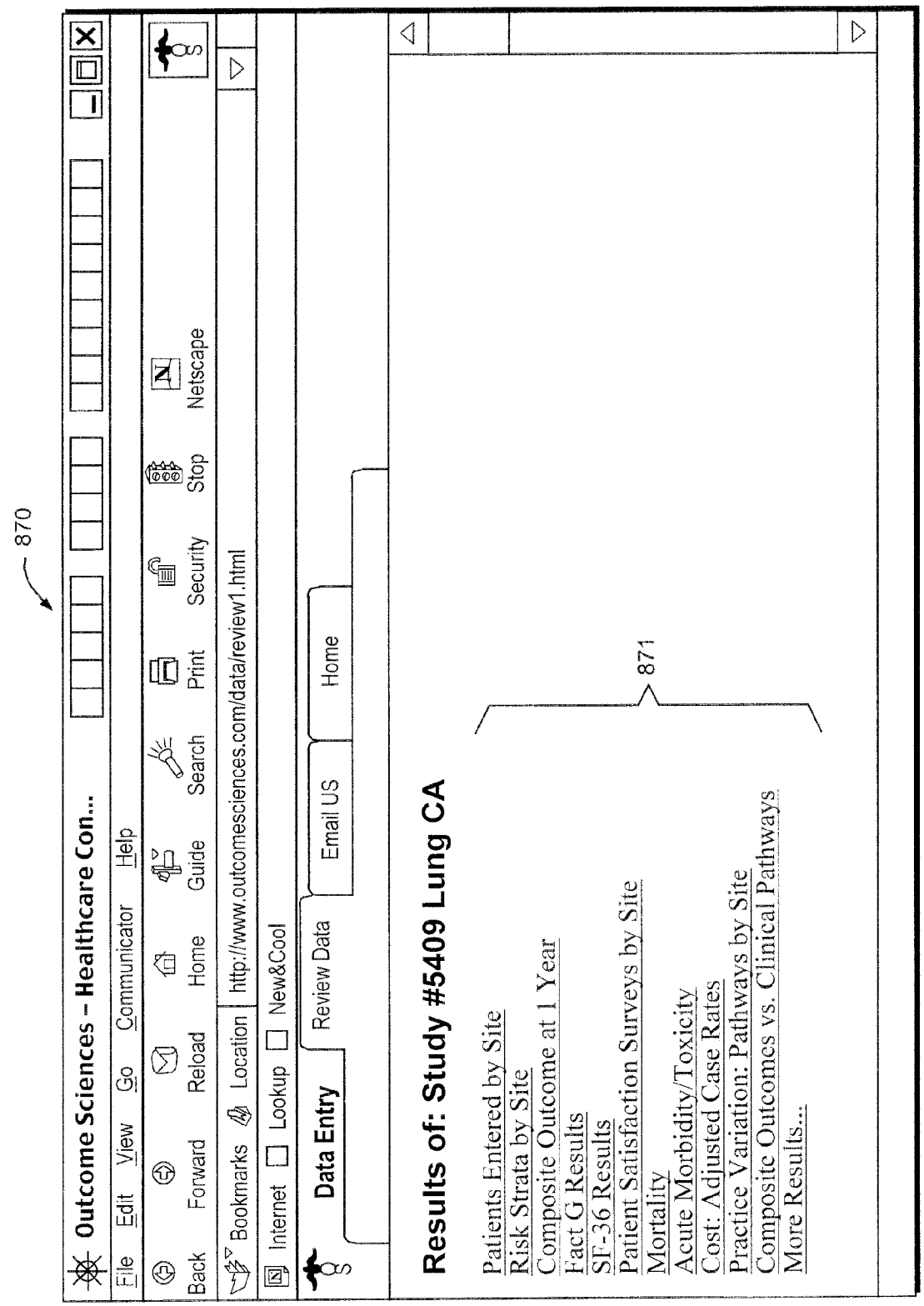
FIG. 15 is a screen shot illustrating a web page interface used to select clinical algorithms and reports that can be generated according to an example embodiment of the invention.
Figure 16A:
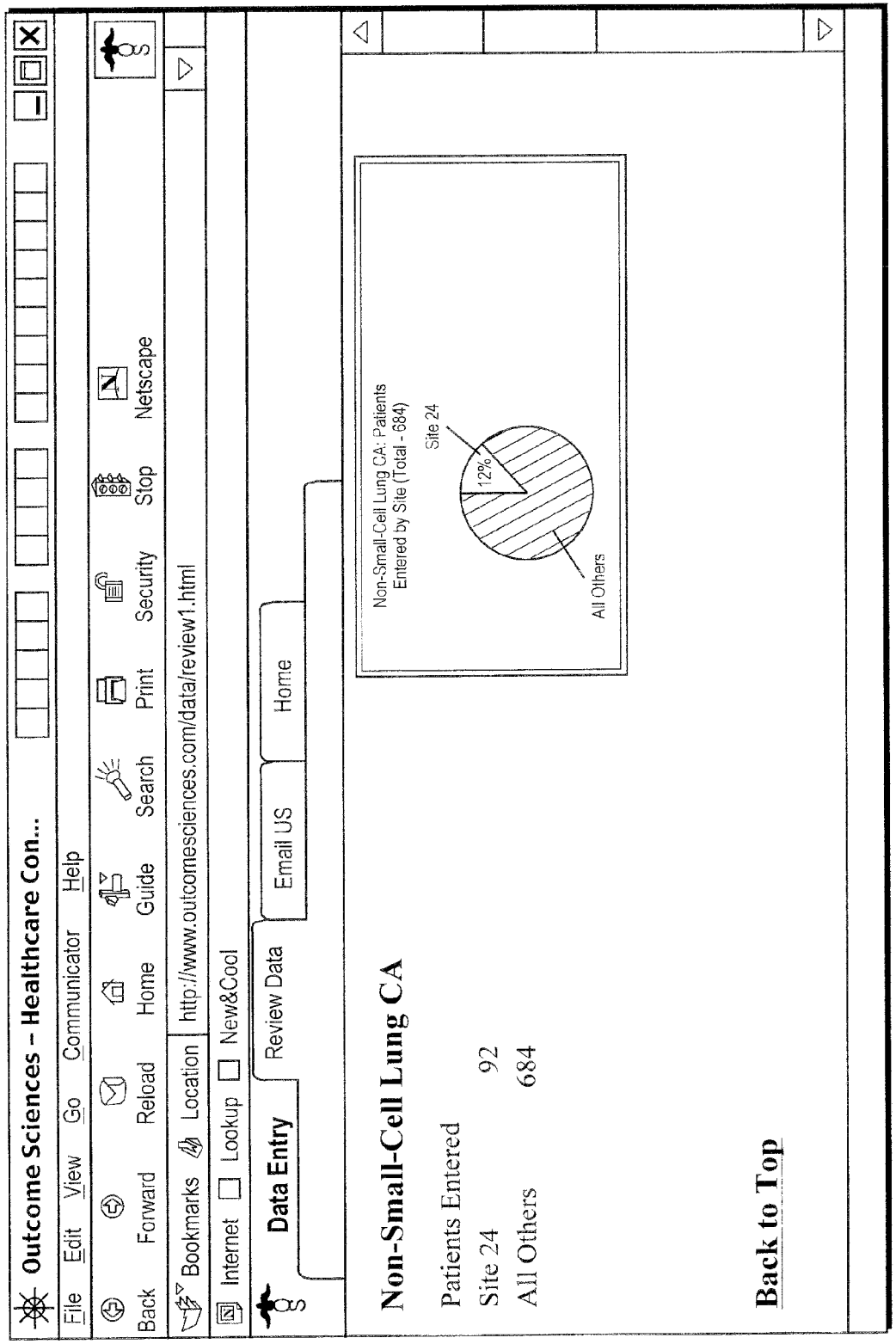
Figure 16C:
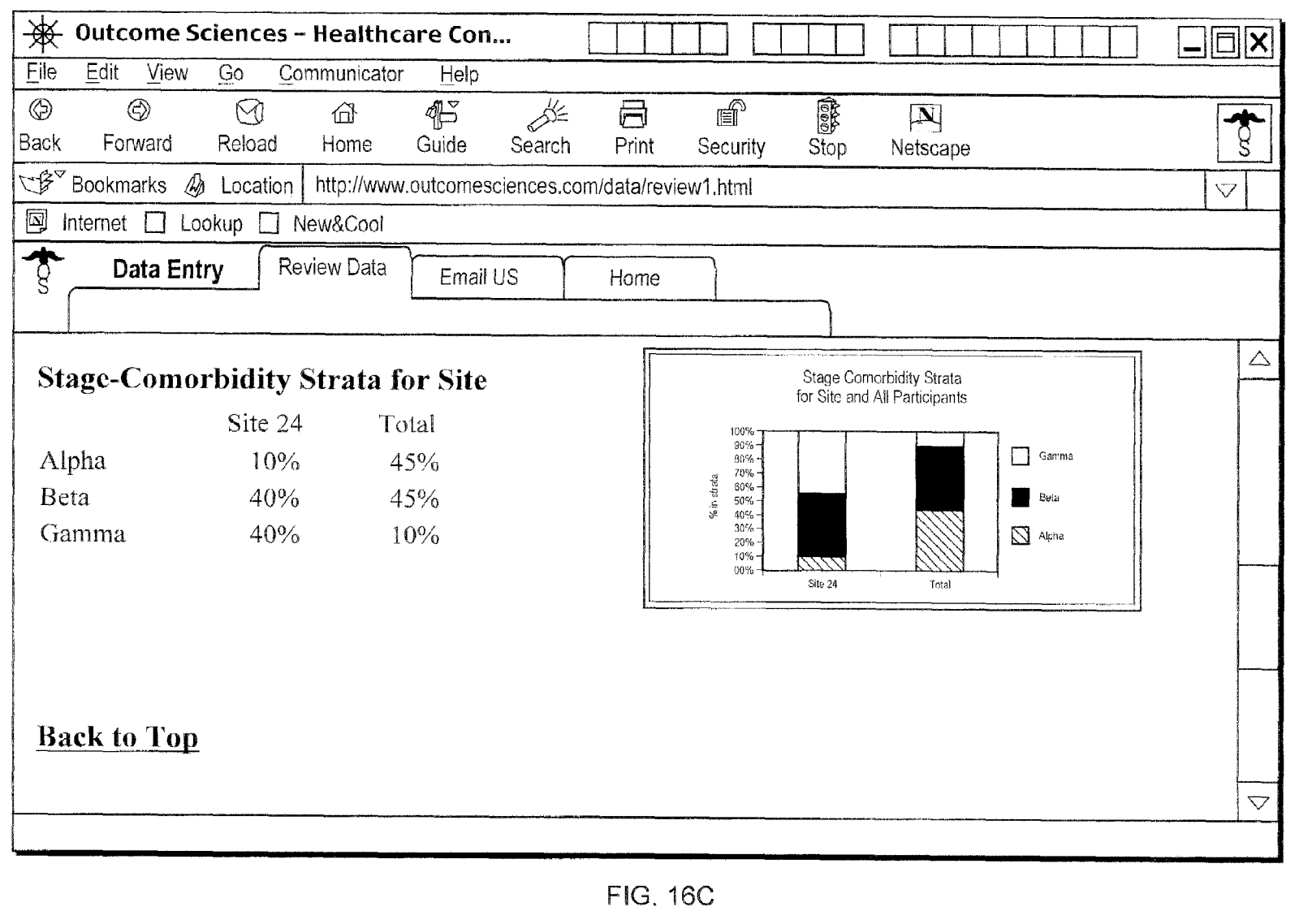
Figure 16E:
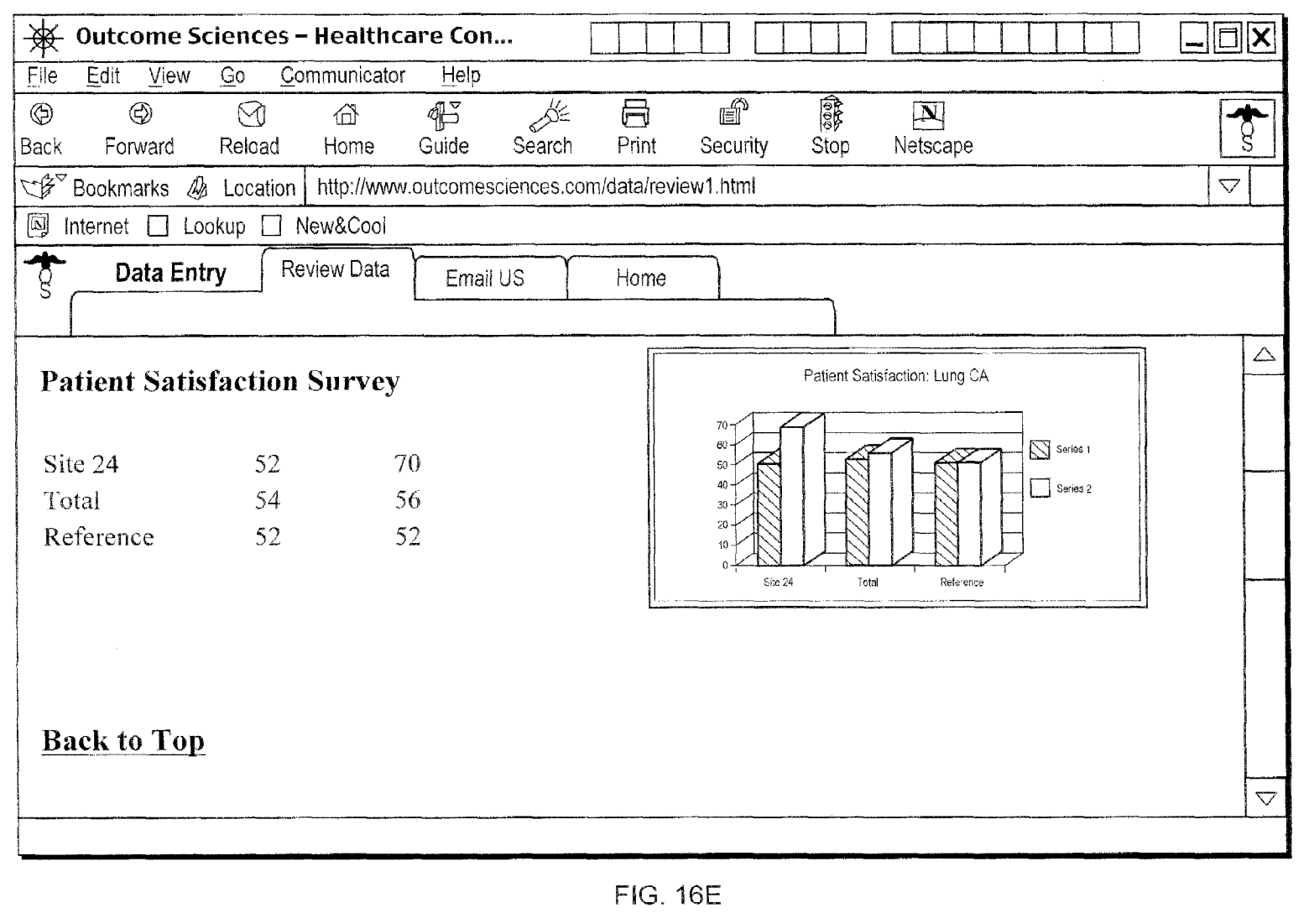
Figure 16G:
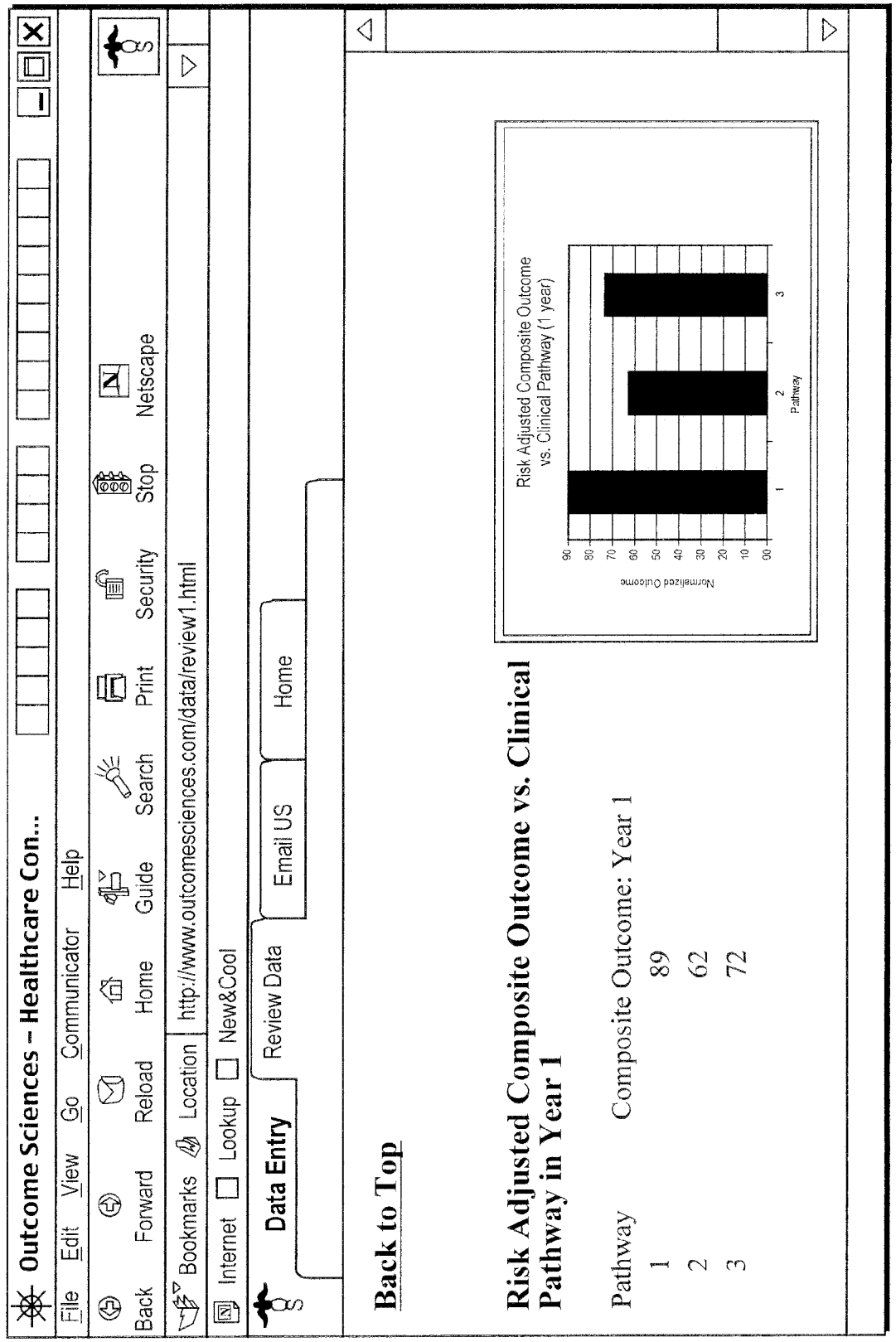

FIGS. 16A through 16F illustrate various example clinical outcome data sets or reports generated by the clinical outcome system 100 when a user selects various clinical algorithm reports 871 from the web page 870 in FIG. 15. Example reports include: patients entered by site (FIG. 16A); composite outcomes for pre- and post-treatment for the study (FIG. 16B); stage-comorbidity strata for a site and all patient participants in the study (FIG. 16C); Quality of Life using SF-36 (a standard measuring technique) (FIG. 16D); Patient satisfaction survey (FIG. 16E), Cost rate per case by strata and site (FIG. 16F); and Risk adjusted composite outcome versus clinical pathway in a specific year of the study (FIG. 16G).

The example clinical algorithms producing outcomes, can for example, provide risk correlations that can be adjusted for baseline risk factors for patients. For example, if a study is used to monitor cancer treatment results, and some patients were smokers while others did not smoke, the correlation may weigh the non-smoker's results more heavily than the smoker's, due to the fact that the person who smokes has a higher risk from dying from a smoking related illness such as heart disease. Such correlations are possible in the invention since the data is collected patient-by-patient and details such as these are available on a widespread basis.

It is to be understood that these reports are merely examples of possible reports and queries that can generated by clinical algorithms produced for the clinical outcome system 100 of this invention. The report data shown in FIGS. 16A through 16G may be saved in the clinical outcome database 414 for use in future research, and can provide a snapshot of the progress of the study thus far.

Since the system of the invention takes into account the most up-to-date medical information to generate each report, as the study evolves, the results of each clinical algorithm report may change as well. Moreover, the clinical algorithms themselves may change to take into account things discovered during the study which should be factored in to the processing of clinical algorithms. Clinical algorithms and studies may be edited, for example, in step 214 in FIG. 5, as explained previously. At the end of a study, the reports generated over time for particular clinical algorithms may be further analyzed to provide a progressive timeline of study development, and may prove useful in and of themselves as research data.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A digital data processing system for determining clinical outcomes of medical data, the digital data processing system comprising:

an input mechanism receiving sets of medical information from at least one user having an associated privilege level, each set of medical information having characteristics relating to a specific medical study and the characteristics of each set having an associated value;

a storage mechanism coupled to the input mechanism, the storage mechanism receiving and maintaining the plurality of sets of medical information;

a processor coupled to the storage mechanism, the processor receiving a selection of a first characteristic and a second characteristic common to at least two sets of medical information, and processing all values of the first and second characteristic according to a clinical algorithm to determine a clinical outcome of the sets of medical information for the specific medical study based upon a comparison of the selected first and second characteristics, wherein the clinical outcome provides an indication of a performance of the doctor for at least one of a specific drug, a specific patient, a specific treatment technique and a specific ailment in comparison to at least one other doctor, the processor configured to determine a relative privilege level of a user; and an output mechanism coupled to the processor to receive the clinical outcome of the sets of medical information and to conditionally output the clinical outcome to the user of the digital data processing system, the processor determining conditional output of the clinical outcome depending upon the associated relative privilege level of the at least one user, such that the at least one user may depend upon the clinical outcome during the course of the medical study and the processor presenting, on the output mechanism, a first user having a higher privilege level a first portion of the clinical outcome and presenting a second user having a lower privilege level a second portion of the clinical outcome, the second portion of the clinical outcome different from the first portion of the clinical outcome.

2. The digital data processing system of claim 1 wherein:
the sets of medical information containing characteristics related to the specific medical study include data related to at least one of a patient, a drug, an ailment, a doctor and a treatment technique; and
wherein a level of processing all values of the first and second characteristic according to a clinical algorithm to determine a clinical outcome is selected based upon the privilege level of the user and wherein the clinical outcome determined based upon the selected first characteristic indicates a statistical result derived from the clinical algorithm for at least one of a patient, a drug, an ailment and a doctor in relation to another of at least one of a patient, a drug, an ailment and a doctor.

3. The digital data processing system of claim 1 wherein the first characteristic is an identity of at least one drug and wherein the second characteristic is an identity of at least one other drug, and wherein the clinical outcome provides an indication of a performance of the at least one drug for treating at least one patient in comparison to the at least one other drug in relation to doctors treating patients.

4. The digital data processing system of claim 1 wherein the first characteristic is an identity at least one first doctor and wherein the second characteristic is an identity of at least one second doctor, and wherein the clinical outcome provides an indication of a performance of the at least one first doctor in comparison to the at least one second doctor as related to at least one of:
  i) treatment of at least one patient;
  ii) treatment of at least one ailment;
  iii) use of at least one drug; and
  iv) the success of at least one surgical technique; and
wherein the digital data processing system comprises:
  means for displaying results of the clinical outcome only if a privilege level of the user is sufficient to allow that user to view the performance of the at least one first doctor in comparison to the at least one second doctor.

5. The digital data processing system of claim 1 wherein the processor instructs the input mechanism to receive specific sets of medical information based upon an identity of a user of the digital data processing system and wherein the clinical algorithm for which all values of the first and second characteristics are processed is selected based upon the identity of the user of the digital data processing system, such that there are two users for which output of the clinical algorithm is different and the two users are a doctor and a director of a medical practice group of doctors that includes the doctor, and wherein the output of the clinical algorithm presented to the doctor is filtered as compared to the output of the same clinical algorithm presented to the director of the group of doctors that includes the doctor.

6. The digital data processing system of claim 1 wherein:
the input mechanism is coupled to a computer network including attached geographically diverse patient and doctor computer systems, and wherein the user of the digital data processing system is a patient who enters at least one of the sets of medical information as input from a patient computer system which is remotely located from the digital data processing system; and
wherein the output mechanism provides only a portion of the clinical outcome to the patient over the network immediately after processing the data, thereby providing the portion of the clinical outcome offering immediate feedback in response to entering patient data that takes into account the most up-to-date sets of medical information, the portion containing only clinical outcome data that the patient is allowed to view based upon the privilege level assigned to the patient.

7. The digital data processing system of claim 1 wherein the processor analyzes the clinical outcome for specific triggering events and notifies at least one of a doctor and an allied medical professional upon detection of a specific triggering event that is determined based on the analysis of the clinical outcome.

8. A method for implementing medical studies, the method comprising the steps of:
  obtaining an identification of a user and an associated privilege level of the user;
  selecting a medical study;
  entering medical data related to a patient associated with the medical study;
  immediately processing the medical data entered in combination with other data associated with the medical study using a clinical algorithm specifically designed for the medical study to produce a clinical outcome of the medical study which takes into account the medical data entered that was related to the patient, wherein the clinical outcome provides an indication of a performance of the doctor for at least one of a specific drug, a specific patient, and a specific ailment in comparison to at least one other doctor;
  determining a relative privilege level of the user; and
  immediately and conditionally, based on the relative privilege level of the user, outputting at least a portion of the clinical outcome data once processed to provide an indication as to how the medical data that was entered for the patient effects, and is related to, the outcome of the medical study in relation to the comparison of doctors, and to present a first user having a higher privilege level a first portion of the clinical outcome and to present a second user having a lower privilege level a second portion of the clinical outcome, the second portion of the clinical outcome different from the first portion of the clinical outcome.

9. The method of claim 8 wherein the step of selecting a medical study includes the steps of:
  presenting to the user a list of medical studies for which that user is associated and to which the privilege level of that user corresponds, thereby focusing attention of the user on particular medical studies;
  allowing the user to select one of the medical studies for which that user is associated; and
  upon a determination that the identification of the user indicates the user is a doctor, then presenting to the doctor a list of patients associated with the medical study and allowing the doctor to select a current patient associated with the medical study and enter a new patient to be associated with the study, and upon a determination that the identification of the user indicates that the user is a medical director, then presenting to the medical director a series of privileged clinical outcome studies that can provide a ranking of doctors against other doctors for the treatment of patients.

10. The method of claim 8 wherein the step of immediately processing the medical data entered using a clinical algorithm executes the clinical algorithm to produce at least one of:
  i) a comparison of doctors for treatment of an ailment;
  ii) a comparison of drugs for treatment of an ailment;
  iii) a comparison of physician groups for treatment of an ailment;

iv) a comparison of surgical techniques for treatment of an ailment; and wherein the method comprises the step of:
displaying results of the clinical outcome only if a privilege level of the user is sufficient to allow that user to view the results of the clinical outcome.

11. The method of claim 8 wherein the step of entering medical data further includes the steps of:
presenting a first question related to the selected medical study to an individual;
retrieving an answer to the question;
presenting a second question related to the selected medical study to the individual, wherein the second question presented is determined by the answer retrieved in response to the first question; and
repeating the steps of presenting a first question, retrieving an answer and presenting a second questions, such that a series of questions are presented to the individual which are governed by the answers received in response to former questions.

12. The method of claim 8 wherein the step of immediately processing the medical data using a clinical algorithm further includes the steps of:
executing the clinical algorithm to determine if the medical data entered does not conform, within a predetermined threshold, to a standardized set of medical data associated with the medical study, and if so, automatically processing a trigger event that prepares a prescription for an individual associated with the medical study.

13. The method of claim 12 wherein the trigger event is processed for a doctor and wherein the processor, in response to processing the trigger event, notifies the doctor that a patient has entered medical data that does not conform to the predetermined threshold of the standardized set of medical data associated with the medical study and wherein the step of preparing a prescription prepares a prescription for a drug for the patient on behalf of the doctor.

14. The method of claim 12 wherein the trigger event is processed for a patient and a doctor and wherein the processor, in response to processing the trigger event, notifies the patient and the doctor that the patient has entered medical data that does not conform to the predetermined threshold of the standardized set of medical data associated with the medical study and that the patient should seek medical treatment and that the doctor should prescribe medical treatment.

15. The method of claim 12 wherein the trigger event is processed based upon an anticipated timing of data entry associated with the medical study and wherein the trigger event automatically processes a prescription on behalf of a doctor treating a patient associated with the trigger event.

16. A computer program product having a computer-readable medium including computer program logic encoded thereon for determining clinical outcomes of medical data, such that the computer program logic, when executed on at least one processing unit with a computing device, causes the at least one processing unit to perform the steps of:
receiving sets of medical information, each set having characteristics relating to a specific medical study and the characteristics of each set having an associated value;
obtaining an identification of a user and an associated privilege level of the user operating the computer system
maintaining the plurality of sets of medical information;
immediately receiving a selection of a first and second characteristics common to at least two sets of medical information, and immediately processing all values of the first and second characteristics according to a clinical algorithm to determine a clinical outcome of the sets of medical information for the specific medical study based upon the selected first characteristic, wherein the clinical outcome provides an indication of a performance of the doctor for at least one of a specific drug, a specific patient, and a specific ailment in comparison to at least one other doctor;
determining a relative privilege level of the user; and
immediately and conditionally, based on the relative privilege level of the user, outputting at least a portion of the clinical outcome to allow the clinical outcome to be used in a state that accounts for the sets of medical information received and to present a first user having a higher privilege level a first portion of the clinical outcome and to present a second user having a lower privilege level a second portion of the clinical outcome, the second portion of the clinical outcome different from the first portion of the clinical outcome.

17. A method performing medical diagnosis, the method comprising the steps of:
receiving sets of computerized medical study data;
receiving an identity of a user having an associated privilege level;
providing feedback used to effect treatment of a patient associated with at least one of the sets of computerized medical data received;
determining a relative privilege level of the user;
generating comparison results describing comparisons of the sets of computerized medical study data to produce a medical study profile, wherein the medical study profile provides an indication of a performance of the doctor for at least one of a specific drug, a specific patient, and a specific ailment in comparison to at least one other doctor and wherein content of the medical study profile is produced at a level according to the relative privilege level of the user and only contains doctor ranking information upon determination that the relative privilege level is sufficiently high enough to allow that user to rank doctors against other doctors and contains ranking of a non-doctor characteristic upon determination that the relative privilege level is not sufficiently high enough to allow that user to rank doctors; and
based on the medical study profile, providing an indication of a ranking of a characteristic of the medical study profile.

18. The method of claim 17 wherein the step of providing an indication of the ranking provides an indication of a risk assessment of any set of computerized medical study data that contains a characteristic that does not conform, within a predetermined threshold, to a standardized characteristic in a typical set of computerized medical study data.

19. The method of claim 18 wherein the step of providing an indication signals a trigger event for at least one of a doctor responsible for treating a patient, and a medical professional associated with the patient, the trigger event notifying the at least one of the patient, the doctor, and the medical professional of the non-conforming characteristic.

20. The method of claim 17 wherein certain of the sets of computerized medical data include a set of answers to a set of questions related to a particular person associated with the medical study; wherein the medical study profile includes a typical set of answers to the set of questions; and wherein the step of generating includes, for each set of computerized medical study data, the step of:

comparing the set of answers related to the particular person to the typical set of answers to the set of questions; and based upon the comparison of the set of answers to the typical set of answers, providing a ranking indicative of a deviation of the set of answers from the typical set of answers.

21. The method of claim 20 wherein the particular person is a doctor having an associated sufficient privilege level and the ranking indicates a relationship of the performance of the doctor in relation to the medical study data in comparison to at least one other doctor.

22. The method of claim 20 wherein the particular person is a patient and the ranking indicates a level of treatment provided to the patient relation to the medical study data for a doctor treating that patient in relation to at least one other doctor.

23. A method for determining clinical outcomes of medical data, the digital data processing system comprising:

receiving sets of medical information, each set having characteristics relating to a specific medical study and the characteristics of each set having an associated value;

receiving an identity of a user having an associated privilege level;

maintaining the plurality of sets of medical information;

determining a relative privilege level of the user;

selecting first and second characteristics common to at least two sets of medical information, and immediately processing all values of the first and the second characteristic, including the first and second characteristic in the sets of medical information received, according to a clinical algorithm to determine a clinical outcome containing privileged information dependent on the relative privilege level of the user, the privileged information including at least one of a risk assessment, a performance rating, and a treatment rating, for the sets of medical information for the specific medical study based upon the selected first and second characteristic to indicate a ranking of at least two doctors in comparison to each other; and immediately outputting the clinical outcome to allow the clinical outcome to be used during the course of the study to effect treatment of a patient associated with at least one of the sets of medical information received based upon the relative privilege level of the user;

wherein the sets of medical information containing characteristics related to the specific medical study include data related to at least one of a patient, a drug, an ailment, a doctor and a treatment technique;

wherein a level of processing all values of the first and second characteristic according to a clinical algorithm to determine a clinical outcome is selected based upon the privilege level of the user and wherein the clinical outcome determined based upon the selected first characteristic indicates a statistical result derived from the clinical algorithm for at least one of a patient, a drug, an ailment and a doctor in relation to another of at least one of a patient, a drug, an ailment and a doctor; and wherein the first characteristic is an identity of at least one drug and wherein the second characteristic is an identity of at least one other drug, and wherein the clinical outcome provides an indication of a performance of the at least one drug for treating at least one patient in comparison to the at least one other drug in relation to doctors treating patients.

24. The method of claim 23 wherein the first characteristic is an identity at least one first doctor and wherein the second characteristic is an identity of at least one second doctor, and wherein the clinical outcome provides an indication of a performance of the at least one first doctor in comparison to the at least one second doctor as related to at least one of:

i) treatment of at least one patient;
ii) treatment of at least one ailment;
iii) use of at least one drug; and
iv) the success of at least one surgical technique wherein the digital data processing system comprises:

means for displaying results of the clinical outcome only if a privilege level of the user is sufficient to allow that user to view the performance of the at least one first doctor in comparison to the at least one second doctor.

25. A method for determining clinical outcomes of medical data, the digital data processing system comprising:

receiving sets of medical information, each set having characteristics relating to a specific medical study and the characteristics of each set having an associated value;

receiving an identity of a user having an associated privilege level, maintaining the plurality of sets of medical information;

determining a relative privilege level of the user;

selecting first and second characteristics common to at least two sets of medical information, and immediately processing all values of the first and the second characteristic, including the first and second characteristic in the sets of medical information received, according to a clinical algorithm to determine a clinical outcome containing privileged information dependent on the relative privilege level of the user, the privileged information including at least one of a risk assessment, a performance rating, and a treatment rating, for the sets of medical information for the specific medical study based upon the selected first and second characteristic to indicate a ranking of at least two doctors in comparison to each other; and immediately outputting the clinical outcome to allow the clinical outcome to be used during the course of the study to effect treatment of a patient associated with at least one of the sets of medical information received based upon the relative privilege level of the user;

wherein the sets of medical information containing characteristics related to the specific medical study include data related to at least one of a patient, a drug, an ailment, a doctor and a treatment technique;

wherein a level of processing all values of the first and second characteristic according to a clinical algorithm to determine a clinical outcome is selected based upon the privilege level of the user and wherein the clinical outcome determined based upon the selected first characteristic indicates a statistical result derived from the clinical algorithm for at least one of a patient, a drug, an ailment and a doctor in relation to another of at least one of a patient, a drug, an ailment and a doctor; and wherein content associated with the clinical outcome that is output is determined, in part, by an identity of a particular person who requests the clinical outcome such that there are two users for which output of the clinical algorithm is different and the two users are a doctor and a director of a medical practice group of doctors that includes the doctor, and wherein the output of the clinical algorithm presented to the doctor is filtered as compared to the output of the same clinical algorithm presented to the director of the group of doctors that includes the doctor.

26. The digital data processing system of claim 1 wherein:
a first user is a medical director and a second user is a doctor under management of the medical director; and
when under control of the medical director, the processor processes all values of the first and second characteristic according to a clinical algorithm to determine a clinical outcome of the sets of medical information that includes privileged information for viewing only by the medical director concerning performance of the doctor; and
when under control of the doctor, the processor processes all values of the first and second characteristic according to a clinical algorithm to determine a clinical outcome of the sets of medical information that does not include privileged information concerning performance of the doctor.

27. The method of claim 8 wherein when processing the medical data to produce a clinical outcome of the medical study, the clinical outcome provides feedback used to effect treatment of a patient associated with the medical study.

28. The digital data processing system of claim 1 wherein the processor is configured to identify respective privilege levels associated with the first user and the second user for purposes of identifying how much of the clinical outcome can be presented to the first user and the second user, both of which can view at least some of the clinical outcome.

29. A method for determining clinical outcomes of medical data, the digital data processing system comprising:
receiving sets of medical information, each set having characteristics relating to a specific medical study and the characteristics of each set having an associated value;
receiving an identity of a user having an associated privilege level;
maintaining the plurality of sets of medical information;
determining a relative privilege level of the user;
selecting first and second characteristics common to at least two sets of medical information, and immediately processing all values of the first and the second characteristic, including the first and second characteristic in the sets of medical information received, according to a clinical algorithm to determine a clinical outcome containing privileged information dependent on the relative privilege level of the user, the privileged information including at least one of a risk assessment, a performance rating, and a treatment rating, for the sets of medical information for the specific medical study based upon the selected first and second characteristic to indicate a ranking of at least two doctors in comparison to each other; and
immediately outputting the clinical outcome to allow the clinical outcome to be used during the course of the study based upon the relative privilege level of the user;
the sets of medical information containing characteristics related to the specific medical study include data related to at least one of a patient, a drug, an ailment, a doctor and a treatment technique; and
wherein a level of processing all values of the first and second characteristic according to a clinical algorithm to determine a clinical outcome is selected based upon the relative privilege level of the user and wherein the clinical outcome determined based upon the selected first characteristic indicates a statistical result derived from the clinical algorithm for at least one of a patient, a drug, an ailment and a doctor in relation to another of at least one of a patient, a drug, an ailment and a doctor; and
wherein the first characteristic is an identity of at least one drug and wherein the second characteristic is an identity of at least one other drug, and wherein the clinical outcome provides an indication of a performance of the at least one drug for treating at least one patient in comparison to the at least one other drug in relation to doctors treating patients.

30. A method for determining clinical outcomes of medical data, the digital data processing system comprising:
receiving sets of medical information, each set having characteristics relating to a specific medical study and the characteristics of each set having an associated value;
receiving an identity of a user having an associated privilege level;
maintaining the plurality of sets of medical information;
determining a relative privilege level of the user;
selecting first and second characteristics common to at least two sets of medical information, and immediately processing all values of the first and the second characteristic, including the first and second characteristic in the sets of medical information received, according to a clinical algorithm to determine a clinical outcome containing privileged information dependent on the relative privilege level of the user, the privileged information including at least one of a risk assessment, a performance rating, and a treatment rating, for the sets of medical information for the specific medical study based upon the selected first and second characteristic to indicate a ranking of at least two doctors in comparison to each other; and
immediately outputting the clinical outcome to allow the clinical outcome to be used during the course of the study based upon the relative privilege level of the user;
the sets of medical information containing characteristics related to the specific medical study include data related to at least one of a patient, a drug, an ailment, a doctor and a treatment technique; and
wherein a level of processing all values of the first and second characteristic according to a clinical algorithm to determine a clinical outcome is selected based upon the relative privilege level of the user and wherein the clinical outcome determined based upon the selected first characteristic indicates a statistical result derived from the clinical algorithm for at least one of a patient, a drug, an ailment and a doctor in relation to another of at least one of a patient, a drug, an ailment and a doctor; and
wherein content associated with the clinical outcome that is output is determined, in part, by an identity of a particular person who requests the clinical outcome such that there are two users for which output of the clinical algorithm is different and the two users are a doctor and a user with a higher privilege level, and wherein the output of the clinical algorithm presented to the doctor is filtered as compared to the output of the same clinical algorithm presented to the user with the higher privilege level.

* * * * *